US012728137B2

(12) United States Patent
Mohapatra et al.

(10) Patent No.: US 12,728,137 B2
(45) Date of Patent: Sep. 8, 2026

(54) METHODS OF TREATING CANCER WITH A COMBINATION OF MITHRAMYCIN AND IMMUNOTHERAPY

(71) Applicant: University of South Florida, Tampa, FL (US)

(72) Inventors: Subhra Mohapatra, Lutz, FL (US); Shyam S. Mohapatra, Lutz, FL (US); Rinku Dutta, Tampa, FL (US); Waise Quarni, Tampa, FL (US)

(73) Assignee: University of South Florida, Tampa, FL (US)

( * ) Notice: Subject to any disclaimer, the term of this patent is extended or adjusted under 35 U.S.C. 154(b) by 957 days.

(21) Appl. No.: 17/642,566

(22) PCT Filed: Oct. 6, 2020

(86) PCT No.: PCT/US2020/054345
§ 371 (c)(1),
(2) Date: Mar. 11, 2022

(87) PCT Pub. No.: WO2021/071800
PCT Pub. Date: Apr. 15, 2021

(65) Prior Publication Data

US 2022/0323467 A1 Oct. 13, 2022

Related U.S. Application Data

(60) Provisional application No. 62/911,544, filed on Oct. 7, 2019.

(51) Int. Cl.
*A61K 31/437* (2006.01)
*A61K 31/704* (2006.01)
*A61K 39/395* (2006.01)
*A61P 35/00* (2006.01)
*A61P 35/04* (2006.01)
*A61K 39/00* (2006.01)

(52) U.S. Cl.
CPC ........ *A61K 31/704* (2013.01); *A61K 39/3955* (2013.01); *A61P 35/00* (2018.01); *A61P 35/04* (2018.01); *A61K 2039/54* (2013.01); *A61K 2039/545* (2013.01)

(58) Field of Classification Search
None
See application file for complete search history.

(56) References Cited

U.S. PATENT DOCUMENTS 8,568,998 B2 10/2013 Mani et al.
2007/0172847 A1 7/2007 Bonavida et al.
2013/0029925 A1 1/2013 Vandier et al.
2013/0101632 A1 4/2013 Scott et al.
2017/0002068 A1 1/2017 Yarden et al.
2018/0051085 A1* 2/2018 Chang ................ C07K 16/2803
2022/0296622 A1* 9/2022 Grohar .................. A61K 45/06

FOREIGN PATENT DOCUMENTS

WO WO 2014083567 6/2014

OTHER PUBLICATIONS

Jia et al (Cancer Research, 2007, 67(10): 4878-4885).*
Msaouel et al (Journal of Clinical Oncology, Feb. 2019, 37; No. 7. Suppl; Abstract #TPS677).*
Miao et al (Nature Genetics, 2018, 50:1271-1281).*
Naito et al (Thoracic Cancer, Apr. 10, 2019, 10:1285-1288).*
Wynja et al (Journal of Immunotherapy, 2018, 41:340-342).*
Agaimy et al (American Journal of Surgical Pathology, 2016, 40:544-553).*
Overman et al (Journal of Clinical Oncology, 2018, 36:773-779).*
National Cancer Institute dictionary, definition of "immunotherapy" (printed Aug. 2025).*
Kasagti et al (Cancer Research, 2016, 76:347-357).*
Jia et al (Cancer Research, 2007, 67:4878-4885).*
Goodman et al (Cancer Immunol. Research, Oct. 1, 2019, 7:1570-1573).*
Ghiringelli et al (Frontiers in Immunology, Aug. 6, 2019, 10:1816, internet pp. 1-10).*
Halama et al (Journal of Clinical Oncology, May 26, 2019; 37:e14143).*
Suzuki et al (American Journal of Cancer Research, 2017, 7:2032-2040).*
Yu et al (Cellular & Molecular Immunology, 2019, 16:401-409; published online Apr. 2018).*
Zhao et al (Oncology Reports, 2013, 30:1782-1792).*
Oladipo et al (British Journal of Cancer, 2011, 104:480-487).*
Hsu et al (International Journal of Molecular Sciences, 2018, 19:2427; internet pp. 1-17).*
Tauriello et al (Nature, 2018, 554:538-543 and Extended Data).*
Schaer et al (Journal of Immuno Therapy of Cancer, 2015, 3(Suppl):p. 402).*
Keedy et al Journal of Clinical Oncology, 2018, 36:3031).*
Jia 2010 (Cancer Research, 2010, 70:1111-1119).*

(Continued)

*Primary Examiner* — Laura B Goddard
(74) *Attorney, Agent, or Firm* — Michele L. Lawson; Shumaker, Loop & Kendrick, LLP

(57) ABSTRACT

The present application is directed to pharmaceutical combinations comprising mithramycin and immunotherapy to target cancer initiating stem cells (CSCs). The present application also discloses methods of treating cancer comprising administering mithramycin and immunotherapy to a subject in need thereof.

4 Claims, 15 Drawing Sheets

(56) References Cited

OTHER PUBLICATIONS

Holmgaard et al (Journal for ImmunoTherapy of Cancer, 2018, 6:47, internet pp. 1-15).*
Gao et al (OncoTargets and Therapy, Aug. 28, 2019, 12:6961-6971).*
Kasagi et al (Cancer Research, 2016, 76:347-357).*
Jia 2007 et al (Cancer Research, 2007, 67:4878-4885).*
Baum (British Journal of Cancer, 22.2 (1968): 176-183).*
Luo et al (BMC Cancer, Feb. 6, 2019, 19: 123; internet pp. 1-13).*
Jiang et al (BMC Cancer, 2015, 15:948, internet pp. 1-10).*
Mao et al (Cancer Management and Research, 2018, 10; 3569-3577).*
Murnane et al (International Journal of Cancer, 209, 2893-2902).*
Zhang et al (Cancer Letters, 2009, 277:114-120).*
Cai et al (Official Journal of Korean Cancer Association 2019;51(1):252-266).*
Zhang et al (Gastroenterology 2010;138:969-980).*
International Preliminary Report on Patentability in International Application No. PCT/US2020/054345, dated Apr. 21, 2022, 8 pages.
Amit M et al., "Upregulation of RET induces perineurial invasion of pancreatic adenocarcinoma," OncogeneJun. 2017, 36(23):3232-3239.
Bailly et al., "Combined cytotoxic Chemotherapy and immunotherapy of cancer: modern terms," NAR Cancer, Feb. 17, 2020, 2(1):1-20.
Bever et al., "An Expanding Role for Immunotherapy in Colorectal Cancer," Journal of the National Comprehensive Cancer Network, 2017,15(3):401-10.
Brahmer et al., "Safety and activity of anti-PD-L1 antibody in subjects with advanced cancer," New England Journal of Medicine, 2012, 366(26):2455-65.
Brown et al., "Mithramycin in the Treatment of Disseminated Testicular Neoplasms," New England Journal of Medicine, Jan. 1965, 272(3):111-118.
Castle et al., "Immunomic, genomic and transcriptomic characterization of CT26 colorectal carcinoma," BMC Genomics, 2014, 15:190, 12 pages.
Chen et al., "Prognostic Value of Cancer Stem Cell Marker ALDH1 Expression in Colorectal Cancer: A Systematic Review and Meta-analysis," PLoS One, 2015, 10(12):e0145164, 15 pages.
Choi et al., "Modulation of specificity protein 1 by mithramycin A as a novel therapeutic strategy for cervical cancer," Scientific Reports, 2014, 4(1):7162, 8 pages.
Chung et al., "Phase II Study of the Anti-Cytotoxic T-Lymphocyte-Associated Antigen 4 Monoclonal Antibody, Tremelimumab, in Patients With Refractory Metastatic Colorectal Cancer," Journal of Clinical Oncology, Jul. 2010, 28(21):3485-3490.
Clarke et al., "Cancer stem cells—perspectives on current status and future directions: AACR Workshop on cancer stem cells," Cancer research, 2006, 66(19):9339-9344.
Das et al., "Actinomycin D Down-regulates SOX2 Expression and Induces Death in Breast Cancer Stem Cells," Anticancer research, 2017, 37(4):1655-63.
Ding K et al., "Artemin, a member of the glial cell line-derived neurotrophic factor family of ligands, is HER2-regulated and mediates acquired trastuzumab resistance by promoting cancer stem cell-like behavior in mammary carcinoma cells," J Biol Chem, Jun. 2014, 289(23):16057-71.
Dutcher et al., "A pilot study of alpha-interferon and plicamycin for accelerated phase of chronic myeloid leukemia," Leukemia Research, 1997, 21(5):375-80.
Efremova et al., "Targeting immune checkpoints potentiates immunoediting and changes the dynamics of tumor evolution," Nature communications, 2018, 9(1):32, 13 pages.
Gao et al., "Neurotrophic Factor Artemin Promotes Invasiveness and Neurotrophic Function of Pancreatic Adenocarcinoma In Vivo and In Vitro," Pancreas, Jan. 2015, 44(1):134-143.
Girard et al., "A 3D fibrous scaffold inducing tumoroids: a platform for anticancer drug development," PLoS One, 2013, 8(10):e75345, pp. 1-11.
Guinney et al., "The consensus molecular subtypes of colorectal cancer," Nature medicine, 2015, 21(11):1350-1356.
Hezam K et al., "Artemin promotes oncogenicity, metastasis and drug resistance in cancer cells," Reviews in the Neurosciences, Jan. 2017, 29(1):93-98.
International Search Report and Written Opinion in International Application No. PCT/US2020/054345, dated Jan. 21, 2021, 10 pages.
Le et al., "PD-1 Blockade in Tumors with Mismatch-Repair Deficiency," N Engl J Med., 2015, 372(26):2509-20.
Lin et al., "Mithramycin A inhibits DNA methyltransferase and metastasis potential of lung cancer cells," Anticancer Drugs, 2007, 18(10):1157-64.
Llosa et al., "The vigorous immune microenvironment of microsatellite instable colon cancer is balanced by multiple counter-inhibitory checkpoints," Cancer Discov, 2015, 5(1):43-51.
Mohapatra et al., "Precision Medicine for CRC Subjects in the Veteran Population: State-of-the-Art, Challenges and Research Directions," Digestive Diseases and Sciences, May 2018, 63(5):1123-1138.
Montico et al., "Immunogenic Apoptosis as a Novel Tool for Anticancer Vaccine Development," International journal of molecular sciences, 2018, 19(2):1-16.
Nagaraj et al., Altered recognition of antigen is a novel mechanism of CD8+ T cell tolerance in cancer, Nature Medicine, Jul. 2007, 13:828-835.
Nair et al., "Three- and Four-dimensional Spheroid and FiSS Tumoroid Cultures: Platforms for Drug Discovery and Development, and Translational Research," Critical reviews in Therapeutic Drug Carrier Systems, 2017, 34 (3):185-208.
Panni et al., Tumor-induced STAT3 activation in monocytic myeloid derived suppressor cells enhances stemness and mesenchymal properties in human pancreatic cancer. Cancer immunology, immunotherapy: CII, 2014, 63(5):513-28.
Peng et al., "Myeloid-Derived Suppressor Cells Endow Stemlike Qualities to Breast Cancer Cells through IL6/STAT3 and NO/NOTCH Cross-talk Signaling," Cancer research, 2016, 76(11):3156-65.
Previdi et al., "Inhibition of Sp1-dependent transcription and antitumor activity of the new aureolic acid analogues mithramycin SDK and SK in human ovarian cancer xenografts," Gynecol Oncol, 2010, 118(2):182-188.
Reya et al., "Stem cells, cancer, and cancer stem cells," Nature, 2001, 414(6859):105-111.
Scatena et al., "Cancer stem cells: the development of new cancer therapeutics," Expert Opin Biological Therapy, 2011, 11(7):875-92.
Signorini et al., "Review on the immunotherapy strategies against metastatic colorectal carcinoma," Immunotherapy, 2016, 8(10):1245-61.
Tauriello et al., "TGFbeta drives immune evasion in genetically reconstituted colon cancer metastasis," Nature, 2018, 554(7693):538-543.
Topalian et al., "Safety, Activity, and Immune Correlates of Anti-PD-1 Antibody in Cancer," New England Journal of Medicine, Jun. 2012, 366(26):2443-2454.
Veglia et al., "Myeloid-derived suppressor cells coming of age," Nature immunology, 2018, 19(2):108-119.
Wohlert et al., "The structure of mithramycin reinvestigated," J Nat Prod, 1999, 62(1):119-21.
Wu et al., "PD-1(+) CD8(+) T cells are exhausted in tumours and functional in draining lymph nodes of colorectal cancer subjects," British Journal of Cancer, Aug. 2014, 111(7):1391-1399.
Yang et al., "Transcription factors Sp1 and Sp3 regulate expression of human ABCG2 gene and chemoresistance phenotype," Molecules and Cells, 2013, 36(4):368-75.
Zhang et al., "Circulating and tumor-infiltrating myeloid-derived suppressor cells in subjects with colorectal carcinoma," PloS one, 2013, 8(2):e57114, pp. 1-10.

(56) References Cited

OTHER PUBLICATIONS

Zhang et al., "Targeting transforming growth factor-beta signaling in liver metastasis of colon cancer," Cancer letters, 2009, 277(1):114-20.

* cited by examiner

HT-29

Mono
Scaffold
E-cadherin/DAPI
αSMA/DAPI
40x
120x
E-Cadherin/DAPI
αSMA/DAPI

CCD841
Mono
Scaf
Fold Change
NANOG
OCT4

SOX2
LGR5
Fold Change
Mono
Scaffold

CT-26
Lgr5
Sox2
Fold Change
Mono
1st
2nd
3rd
Scaffold

HCT-116
Monolayer
Scaffold
SSC-A
12.5%
63.4%
DEAB
0.5%
0.1%
ALDE Fluor Intensity

| HCT116 | Calreticulin (%) |
|---|---|
| 0nm | 22.5% |
| 10nm | 19.2% |
| 20nm | 36.2% |
| 40nm | 38.3% |
| 80nm | 41.4% |

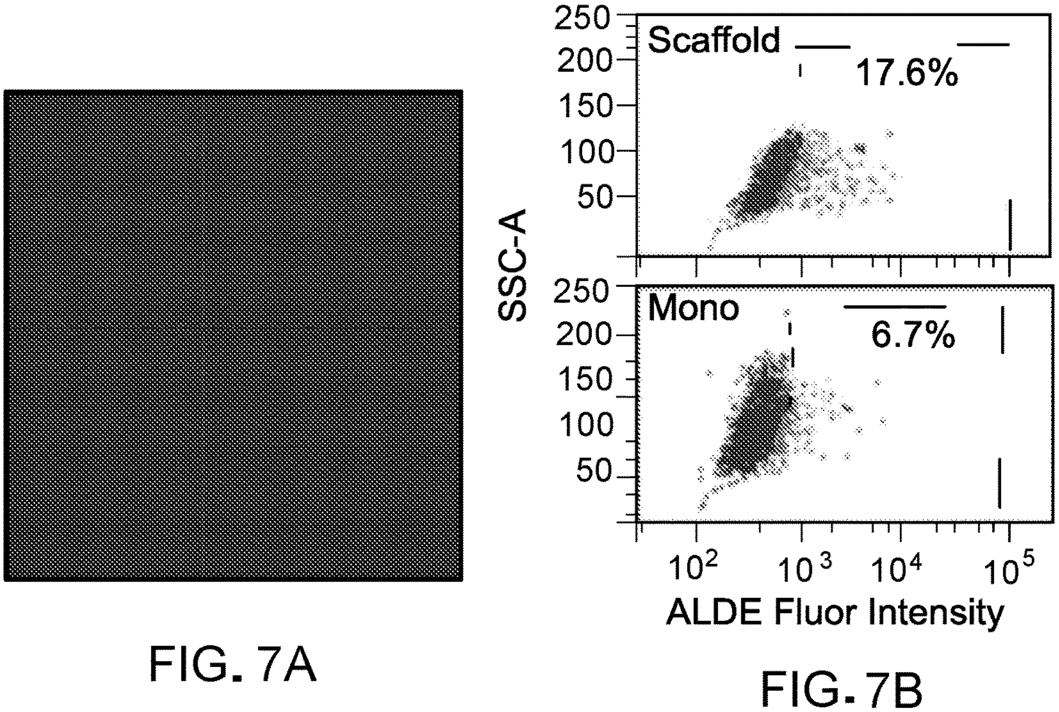
FIG. 7A
FIG. 7B
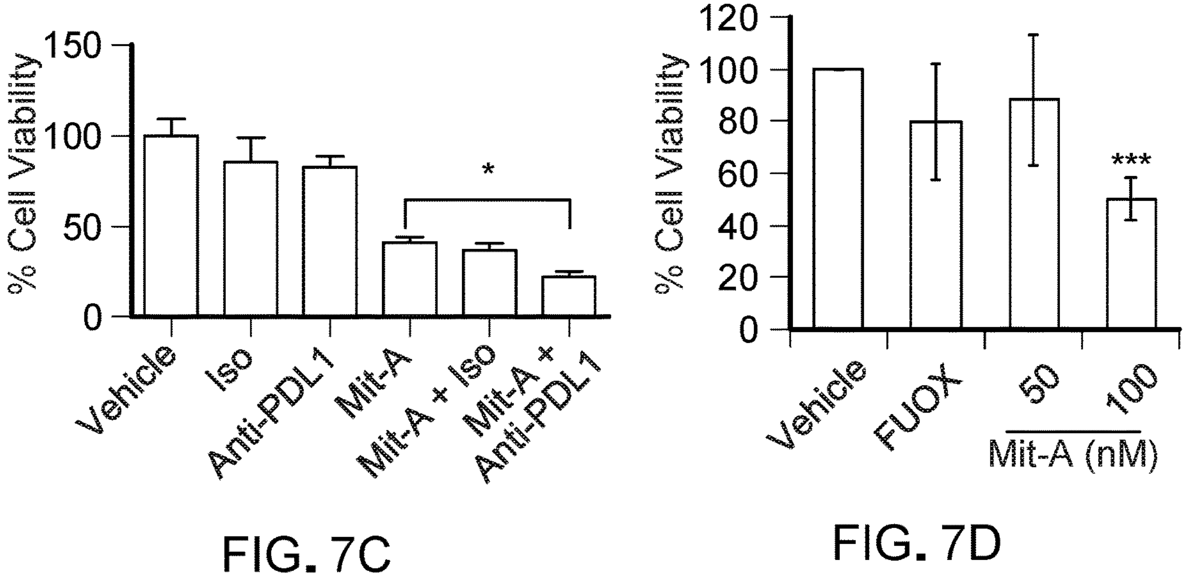
FIG. 7C
FIG. 7D

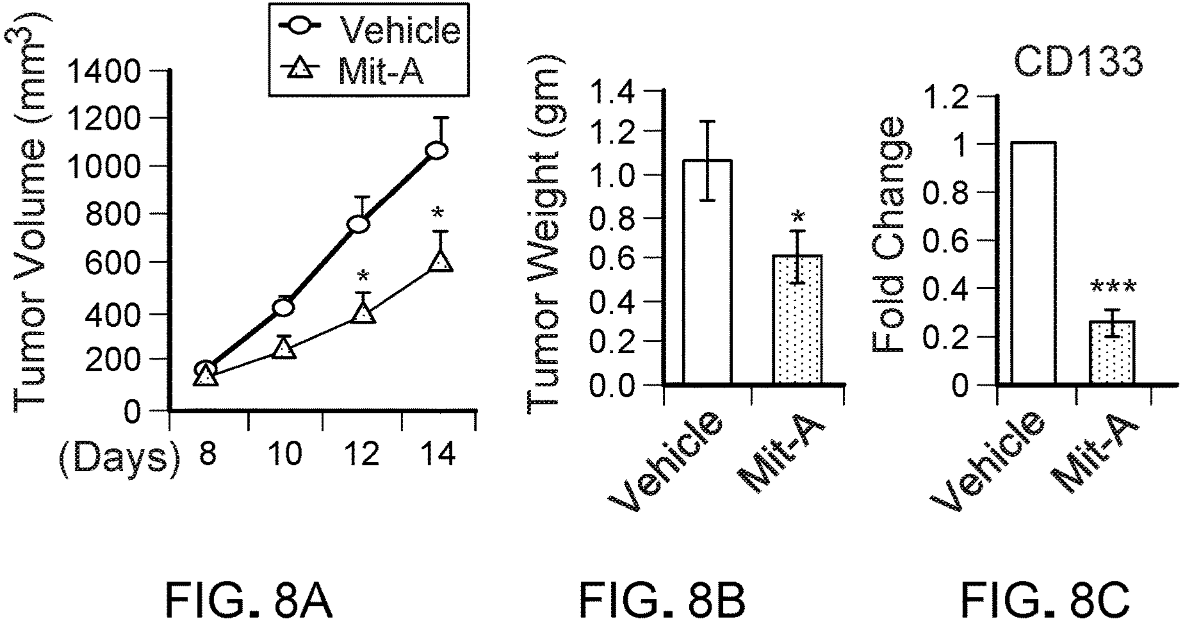
FIG. 8A
FIG. 8B
FIG. 8C
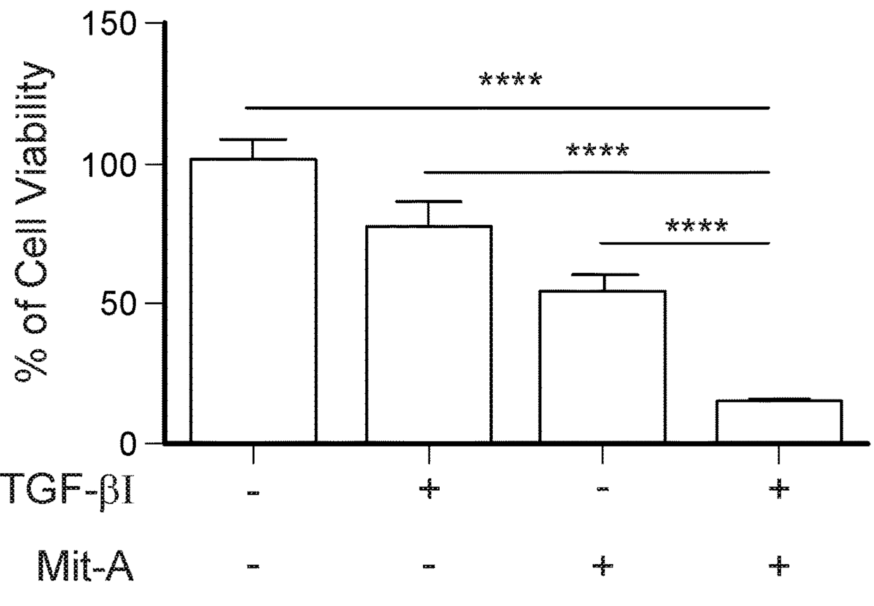
FIG. 9

Tumor Weight (g)

*

***

****

****

V I P M M+P

METHODS OF TREATING CANCER WITH A COMBINATION OF MITHRAMYCIN AND IMMUNOTHERAPY

CROSS-REFERENCE TO RELATED APPLICATIONS

This application is a U.S. National Phase Application of International Application No. PCT/US2020/054345, filed on Oct. 6, 2020, which claims priority to U.S. Provisional Application No. 62/911,544, filed on Oct. 7, 2019, both of which are incorporated by reference in their entirety.

STATEMENT OF FEDERALLY SPONSORED RESEARCH

This invention was made with government support under Grant no. BX003413, awarded by the US Department of Veterans Affairs. The government has certain rights in the invention.

TECHNICAL FIELD

This invention relates to methods and compositions for treating cancer, and more particularly to combinations of mithramycin and immunotherapy.

BACKGROUND

The present disclosure relates to novel combinations for treating cancer, pharmaceutical compositions comprising the therapeutic agents, and the use of the combinations in therapy. More particularly, it relates to mithramycin in combination with cancer immunotherapy, which is useful in the treatment and prevention of cancer.

Self-renewal and plasticity of cancer initiating stem cells (CSCs) is regulated by interaction with: i) cancer-associated fibroblasts (CAFs), and ii) immune cells such as lymphocytes, dendritic cells (DCs), myeloid-derived suppressor cells (MDSCs), and macrophages (MΦ) in the onc-immune microenvironment (OIM). CSCs are often referred to as the seed of tumors, playing a central role in processes such as tumor initiation and growth, invasion, metastasis, and development of drug resistance and cancer relapse [1, 2]. Therefore, therapeutic strategies which specifically target CSCs can improve the efficacy of cancer therapy and provide a sustained and durable response.

The role of CSC-immune interactions in OIM remains poorly understood. Among immune cells, MDSCs constitute one of the major mechanisms of tumor escape from immune control as well as an important factor limiting the success of cancer immunotherapy (CIx)[3]. MDSCs play an important role in tumor non-responsiveness by suppressing T cell responses by secreting nitric oxide (NO), reactive oxygen species (ROS), arginase, IL-10 and IL-6, and via engagement of programmed cell death 1 (PD-1) and its ligand (PD-L1)[4, 5]. MDSCs also promote CSC expansion via STAT3 and NOTCH signaling and IL-6[6-8]. Like MDSCs, CSCs can also down-regulate T cell immunity through PD-1: PD-L1 interaction. Hence, a novel CIx, which specifically targets CSCs in the OIM may inhibit MDSC-mediated immune suppression by redirecting differentiation of MDSCs to monocytic MDSCs (m-MDSCs) rather than granulocytic (PMN) MDSCs (g-MDSCs), leading to enhanced anti-tumor immune response.

In an effort to recapitulate the in vivo OIM, herein a novel ex vivo CIx testing platform has been developed using a recently pioneered polymeric nanofiber-inspired smart 3D scaffold (FiSS), on which culture of tumor tissues and biopsy cells leads to formation of tumor-like organoids, referred to as tumoroids, with molecular signatures of solid tumors[9-11]. It is planned to extend this tumoroid platform to incorporate autologous immune cells to form an ex vivo CSC immune cell tumoroid (CIT) platform and test its potential to modulate CIx.

A FiSS-based tumoroid platform has been developed on which tumor cells readily form tumor-like structures, tumoroids, which exhibit epithelial to mesenchymal transition (EMT) and resemble in vivo tumors in drug-responsiveness[9-11]. The uniqueness of the tumoroid cultures lies in their ability to substantially expand CSCs, as determined by CSC biomarker expression and CSC activity assayed by measurement of aldehyde dehydrogenase (ALDH) activity. Since CSC phenotype in human colon cancer is associated with poor prognosis[12, 13], a number of therapeutic approaches targeting CSCs are under investigation. These include either inhibition of self-renewal or induction of differentiation[2,14] using small molecules such as the kinase inhibitors and several polypeptide inhibitors. An NCI library of FDA-approved drugs was screened using colorectal cancer (CRC)-tumoroid platform and sphere formation assay, which revealed that a class of antibiotic drugs including mithramycin A (Mit-A) are the most potent inhibitors of CSC. Of note, Mit-A has been approved as an antineoplastic drug since 1970[15,16] and has been implicated in regulating transcription factor Sp1, which is involved in chemoresistant cancers[17].

In case of CRCs, a subset of subjects with mismatch repair-deficient (microsatellite high or MSI-H) tumors is highly responsive to immune checkpoint inhibitors (ICIs) with a good prognosis[18]. However, such therapy is not adequate for microsatellite stable (MSS) carcinomas, which comprise the bulk of the aggressive CRCs with poor outcomes[19]. Hence, new treatment approaches are being sought for MSS colon tumors. Most of the CIx can be grouped as ICIs like anti-cytotoxic T-lymphocyte-associated antigen-4 (αCTLA-4)[20], anti-PD-1 (αPD-1)[21], anti-PD-L1 (αPD-L1)[22]. Currently CIx trials (46 actively recruiting) target highly expressed tumor antigens like CEA, APC, MAGE, MUC-1, and SURVIVIN, or common mutations in the WNT, MAPK, P53 or apoptosis pathway[23, 24].

CIX is an emerging effective modality for CRC; however, for a majority of subject with MSS carcinoma, CIx has not been adequately effective. While CIx kills tumor cells, it does not provide durable response due to the presence of CSCs that are responsible for their relapse. Thus, treatment strategies for addressing these aggressive CRCs are needed.

SUMMARY

This application is based, in part, on the surprising and unexpected discovery that combining Mit-A with cancer immunotherapy (e.g., αPD-L1) significantly increases the effectiveness of the latter in an immunocompetent MC-38 CRC tumor model.

The details of one or more embodiments of the invention are set forth in the accompanying drawings and the description below. Other features, objects, and advantages of the invention will be apparent from the description and drawings, and from the claims.

Provided herein are methods of treating cancer, comprising administering (a) mithramycin, or a pharmaceutically acceptable salt thereof, and (b) an immunotherapy, to a subject that has been diagnosed with cancer; and wherein the amounts of (a) and (b) together are effective in treating the cancer.

Also provided herein are methods of treating cancer, comprising administering (a) mithramycin, or a pharmaceutically acceptable salt thereof, and (b) an immunotherapy, to a subject in need thereof.

Also provided herein are methods of inhibiting metastasis of a cancer in a subject in need thereof, the method comprising administering to the subject (a) mithramycin, or a pharmaceutically acceptable salt thereof, and (b) an immunotherapy; wherein the amounts of (a) and (b) together are effective in inhibiting metastasis.

Also provided herein are methods of inhibiting metastasis of a cancer in a subject in need thereof, the method comprising administering to the subject (a) mithramycin, or a pharmaceutically acceptable salt thereof, and (b) an immunotherapy.

Further provided herein are methods of inhibiting mammalian cell proliferation, comprising contacting the mammalian cell with (a) mithramycin, or a pharmaceutically acceptable salt thereof, and (b) and immunotherapy; wherein the amounts of (a) and (b) together are effective in inhibiting mammalian cell proliferation.

Further provided herein are methods of inhibiting mammalian cell proliferation, comprising contacting the mammalian cell with (a) mithramycin, or a pharmaceutically acceptable salt thereof, and (b) and immunotherapy.

Also provided herein are pharmaceutical compositions comprising mithramycin, or a pharmaceutically acceptable salt thereof, an immunotherapy, and at least on pharmaceutically acceptable excipient.

DESCRIPTION OF DRAWINGS

FIG. 7A depicts an image of Nuc-blue stained MC38 tumoroids. FIG. 7B depicts the ALDH activity measured using the ALDE Fluor kit in monolayer (bottom panel) compared to scaffold cultured MC38 tumor cells (top panel). FIG. 7C depicts a bar graph of cell viability of MC38 tumoroids as assayed by CellTiter-Glo. FIG. 7D depicts a bar graph of cell viability of MC38 tumoroids as assayed by CellTiter-Glo.

FIG. 8A depicts a bar graph of tumor volume measured on indicated days using a caliper after treatment with Mit-A. FIG. 8B depicts a bar graph of tumor weight recorded on day 16. FIG. 8C depicts a bar graph of CD133 expression analyzed by qPCR.

FIG. 9 depicts a bar graph of cell viability assayed by CellTiter-Glo of CT26 cells that were cultured in the presence of TGFβI, LY2109761 (5 μM) and/or 150 nM Mit-A for 48 hrs.

DETAILED DESCRIPTION

Figures 1A, 1B, 1C, 1D, 1E, 1F, 1G, 1H:
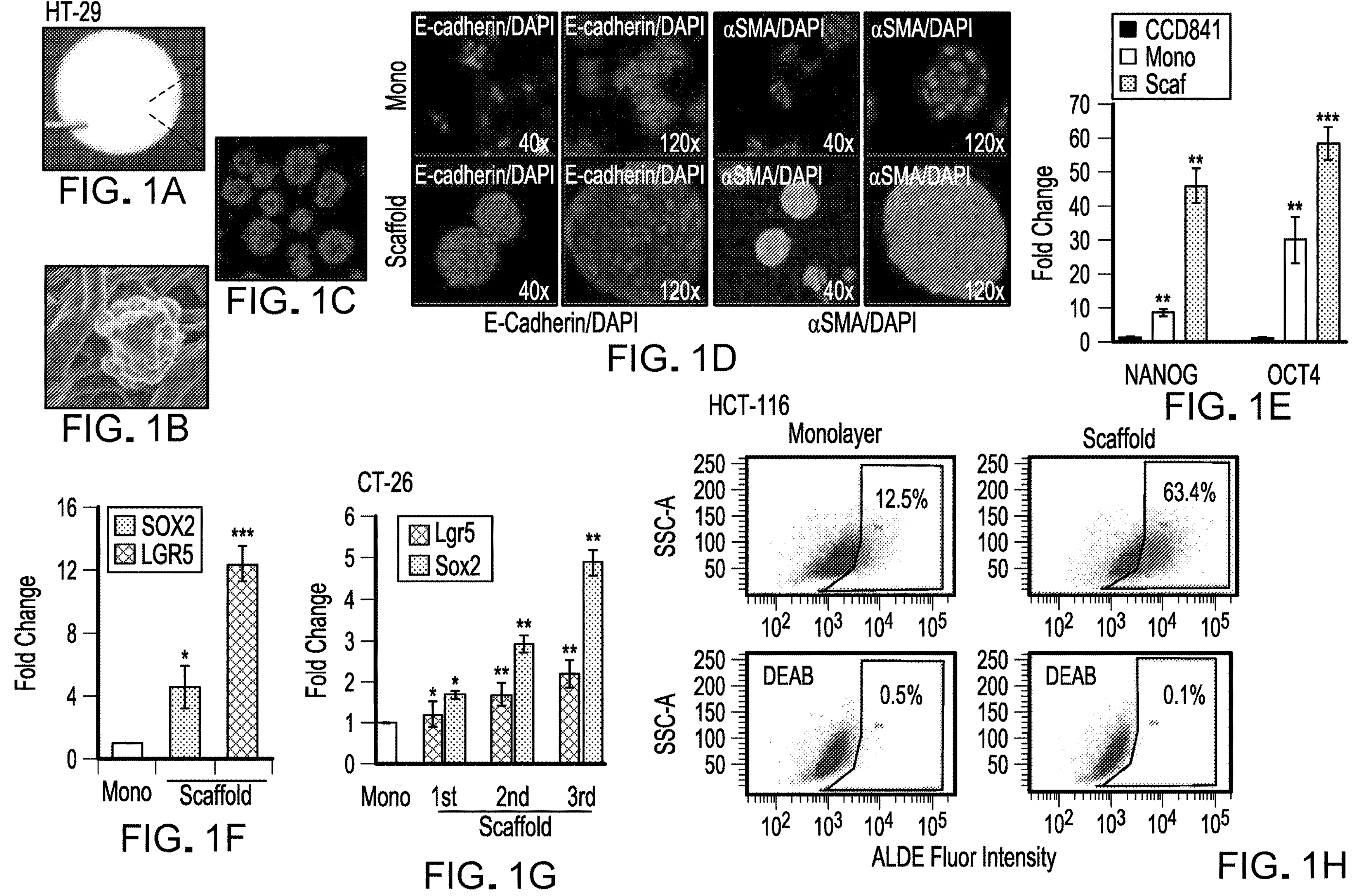
FIG. 1A depicts an image of a scaffold matrix held by forceps tip.
FIG. 1B depicts a scanning electron microscope image (EM) of Day 4 HT-29 tumoroid on the scaffold.
FIG. 1C depicts Nuc Blue-stained HT-29 tumoroids in culture.
FIG. 1D depicts HT-29 tumoroids that developed features of EMT (decreased E-cadherin and increased α-smooth muscle actin (SMA)) shown by immunofluorescence (IF) staining after 6 days of culture.
FIG. 1E depicts a bar graph showing a qPCR comparison between normal human colon cell CCD841 to colon cancer cell HT29 grown on monolayer and scaffold.
FIG. 1F depicts qPCR of HT29 grown on monolayer vs. scaffolds.
FIG. 1G depicts a qPCR of CT26 grown on monolayer and scaffolds for 3 consecutive passages.
FIG. 1H depicts the ALDH activity of HCT116 monolayer and scaffold measured using the ALDE Fluor kit (Stem Cell Technologies).

Some embodiments provide a method of treating cancer, comprising administering (a) mithramycin, or a pharmaceutically acceptable salt thereof, and (b) an immunotherapy, to a subject in need thereof.

Some embodiments provide a method of treating cancer, comprising administering (a) mithramycin, or a pharmaceutically acceptable salt thereof, and (b) an immunotherapy, to a subject that has been diagnosed with cancer; and wherein the amounts of (a) and (b) together are effective in treating the cancer.

Some embodiments provide a method of treating cancer, comprising administering (a) mithramycin, or a pharmaceutically acceptable salt thereof, and (b) pembrolizumab, to a subject in need thereof.

Some embodiments provide a method of treating cancer, comprising administering (a) mithramycin, or a pharmaceutically acceptable salt thereof, and (b) pembrolizumab, to a subject that has been diagnosed with cancer; and wherein the amounts of (a) and (b) together are effective in treating the cancer.

Some embodiments provide a method of treating cancer, comprising administering (a) mithramycin, or a pharmaceutically acceptable salt thereof, and (b) nivolumab, to a subject in need thereof.

Some embodiments provide a method of treating cancer, comprising administering (a) mithramycin, or a pharmaceutically acceptable salt thereof, and (b) nivolumab, to a subject that has been diagnosed with cancer; and wherein the amounts of (a) and (b) together are effective in treating the cancer.

In some embodiments, the diagnosing of cancer comprises obtaining a sample from the subject and performing an assay on the sample. In some embodiments, the sample is a biopsy sample. In some embodiments, the assay is selected from the group consisting of sequencing, immunohistochemistry, enzyme-linked immunosorbent assay, and fluorescence in situ hybridization (FISH).

In some embodiments, the cancer is a lung cancer or a colorectal cancer. In some embodiments, the cancer is a lung cancer. In other embodiments, the cancer is a colorectal cancer. In some embodiments, the colorectal cancer is selected from adenocarcinoma, gastrointestinal carcinoid tumor, gastrointestinal stromal tumor (GIST), primary colorectal lymphoma, and a sarcoma.

In some embodiments, the expression of one or more inflammatory factors in the subject is inhibited. In some embodiments, the expression of the one or more inflammatory factors in the subject is inhibited by about 10% to about 95%, for example, about 10% to about 30%, about 30% to about 50%, about 50% to about 70%, about 70% to about 95%, about 10%, about 20%, about 30%, about 40%, about 50%, about 60%, about 70%, about 80%, about 90%, or about 95%. In some embodiments, the one or more inflammatory factors are selected from CXCL1, MIP3α, MMP2, TPO, E-selectin, Leptin-R, IL-3, and IL-10. In some embodiments, the one or more inflammatory factors are associated with a metastatic colorectal cancer. In some embodiments, the one or more inflammatory factors are independently selected from CXCL1, MIP3α, MMP2, and TPO. In some embodiments, the one or more inflammatory factors are associated with increased tumor cell migration. In some embodiments, the one or more inflammatory factors include E-selectin. In some embodiments, the one or more inflammatory factors are associated with neoangiogenesis. In some embodiments, the one or more inflammatory factors include leptin-R. In some embodiments, the one or more inflammatory factors are selected from IL-3 and IL-10. In some embodiments, the one or more inflammatory factors are independently selected from E-selectin, leptin-R, CXCL1, MIP3α, MMP2, and TPO.

In some embodiments, a reduction in Ki-67 and/or Lgr5 expression occurs in the subject. In some embodiments, the expression is reduced by about 10% to about 95%, for example, about 10% to about 30%, about 30% to about 50%, about 50% to about 70%, about 70% to about 95%, about 10%, about 20%, about 30%, about 40%, about 50%, about 60%, about 70%, about 80%, about 90%, or about 95%. In some embodiments, E-cadherin, IL12 p70, and/or Granzyme B expression is increased in the subject. In some embodiments, the expression is increased by about 10% to about 95%, for example, about 10% to about 30%, about 30% to about 50%, about 50% to about 70%, about 70% to about 95%, about 10%, about 20%, about 30%, about 40%, about 50%, about 60%, about 70%, about 80%, about 90%, or about 95%.

Some embodiments provide a method of inhibiting metastasis of a cancer in a subject in need thereof, the method comprising administering to the subject (a) mithramycin, or a pharmaceutically acceptable salt thereof, and (b) an immunotherapy. Some embodiments provide a method of inhibiting metastasis of a cancer in a subject in need thereof, the method comprising administering to the subject (a) mithramycin, or a pharmaceutically acceptable salt thereof, and (b) an immunotherapy; wherein the amounts of (a) and (b) together are effective in inhibiting metastasis.

Some embodiments provide a method of inhibiting metastasis of a cancer in a subject in need thereof, the method comprising administering to the subject (a) mithramycin, or a pharmaceutically acceptable salt thereof, and (b) pembrolizumab. Some embodiments provide a method of inhibiting metastasis of a cancer in a subject in need thereof, the method comprising administering to the subject (a) mithramycin, or a pharmaceutically acceptable salt thereof, and (b) pembrolizumab; wherein the amounts of (a) and (b) together are effective in inhibiting metastasis.

Some embodiments provide a method of inhibiting metastasis of a cancer in a subject in need thereof, the method comprising administering to the subject (a) mithramycin, or a pharmaceutically acceptable salt thereof, and (b) nivolumab. Some embodiments provide a method of inhibiting metastasis of a cancer in a subject in need thereof, the method comprising administering to the subject (a) mithramycin, or a pharmaceutically acceptable salt thereof, and (b) nivolumab; wherein the amounts of (a) and (b) together are effective in inhibiting metastasis.

In some embodiments, the cancer is at high risk of developing metastasis. In some embodiments, the cancer is a lung cancer or a colorectal cancer. In some embodiments, the cancer is a lung cancer. In other embodiments, the cancer is a colorectal cancer. In some embodiments, the colorectal cancer is selected from adenocarcinoma, gastrointestinal carcinoid tumor, gastrointestinal stromal tumor (GIST), primary colorectal lymphoma, and a sarcoma. In some embodiments, the metastasis is a central nervous system metastasis.

In some embodiments, the immunotherapy comprises an immune checkpoint inhibitor. In some embodiments, the immunotherapy modulates (e.g., inhibits) PD-1 or α-PD-L1. In some embodiments, the immunotherapy comprises an anti-PD-1 and/or an anti-α-PD-L1 monoclonal antibody. In some embodiments, the immunotherapy is selected from alemtuzumab, atezolizuman, avelumab, ipilimumab, ofatumumab, nivolumab, pembrolizumab, cemiplimab, rituximab, and durvalumab. In some embodiments, the immunotherapy is nivolumab or pembrolizumab. In some embodiments, the mithramycin, or a pharmaceutically acceptable salt thereof, is administered orally. In some embodiments, the immunotherapy is administered parenterally. In some embodiments, the mithramycin, or a pharmaceutically acceptable salt thereof, and the immunotherapy are administered at substantially the same time. In some embodiments, the mithramycin, or a pharmaceutically acceptable salt thereof, and the immunotherapy are administered sequentially, in either order. In some embodiments, the mithramycin, or a pharmaceutically acceptable salt thereof, and the immunotherapy are administered on different dosing schedules, as described herein.

In some embodiments, the mithramycin, or a pharmaceutically acceptable salt thereof, is administered at a dose of about 0.5 mg/kg to about 10.0 mg/kg of any value in between; for example, about 0.5 mg/kg to about 1.5 mg/kg, about 1 mg/kg to about 2 mg/kg, about 1.5 mg/kg to about 2.5 mg/kg, about 2 mg/kg to about 3 mg/kg, about 2.5 mg/kg to about 3.5 mg/kg, about 3 mg/kg to about 4 mg/kg, about 3.5 mg/kg to about 4.5 mg/kg, about 4 mg/kg to about 5 mg/kg, about 4.5 mg/kg to about 5.5 mg/kg, about 5 mg/kg to about 6 mg/kg, about 5.5 mg/kg to about 6.5 mg/kg, about 6 mg/kg to about 7 mg/kg, about 6.5 mg/kg to about 7.5 mg/kg, about 7 mg/kg to about 8 mg/kg, about 7.5 mg/kg to about 8.5 mg/kg, about 8 mg/kg to about 9 mg/kg, about 8.5 mg/kg to about 9.5 mg/kg, about 9 mg/kg to about 10 mg/kg, or any value in between.

In some embodiments, the immunotherapy is administered at a standard dose, for example, the dose recommended on a package insert and/or product label, as prescribed by a physician.

In some embodiments, the mithramycin, or a pharmaceutically acceptable salt thereof, is administered daily. In other embodiments, the mithramycin, or a pharmaceutically acceptable salt thereof, is administered every other day. In still other embodiments, the mithramycin, or a pharmaceutically acceptable salt thereof, is administered weekly.

In some embodiments, the immunotherapy is administered daily. In other embodiments, the immunotherapy is administered every other day. In still other embodiments, the immunotherapy is administered weekly. In some embodiments, the immunotherapy is administered in one or more cycles, wherein each cycle comprises administration of the immunotherapy once every three weeks. In some embodiments, the immunotherapy is administered over 3-10 cycles. In other embodiments, the immunotherapy is administered over 3-6 cycles.

In some embodiments, the expression of one or more inflammatory factors in the subject is inhibited. In some embodiments, the expression of the one or more inflammatory factors in the subject is inhibited by about 10% to about 95%, for example, about 10% to about 30%, about 30% to about 50%, about 50% to about 70%, about 70% to about 95%, about 10%, about 20%, about 30%, about 40%, about 50%, about 60%, about 70%, about 80%, about 90%, or about 95%. In some embodiments, the one or more inflammatory factors are selected from CXCL1, MIP3α, MMP2, TPO, E-selectin, Leptin-R, IL-3, and IL-10. In some embodiments, the one or more inflammatory factors are associated with a metastatic colorectal cancer. In some embodiments, the one or more inflammatory factors are independently selected from CXCL1, MIP3α, MMP2, and TPO. In some embodiments, the one or more inflammatory factors are associated with increased tumor cell migration. In some embodiments, the one or more inflammatory factors include E-selectin. In some embodiments, the one or more inflammatory factors are associated with neoangiogenesis. In some embodiments, the one or more inflammatory factors include leptin-R. In some embodiments, the one or more inflammatory factors are selected from IL-3 and IL-10. In some embodiments, the one or more inflammatory factors are independently selected from E-selectin, leptin-R, CXCL1, MIP3α, MMP2, and TPO.

In some embodiments, a reduction in Ki-67 and/or Lgr5 expression occurs in the subject. In some embodiments, the expression is reduced by about 10% to about 95%, for example, about 10% to about 30%, about 30% to about 50%, about 50% to about 70%, about 70% to about 95%, about 10%, about 20%, about 30%, about 40%, about 50%, about 60%, about 70%, about 80%, about 90%, or about 95%. In some embodiments, E-cadherin, IL12 p70, and/or Granzyme B expression is increased in the subject. In some embodiments, the expression is increased by about 10% to about 95%, for example, about 10% to about 30%, about 30% to about 50%, about 50% to about 70%, about 70% to about 95%, about 10%, about 20%, about 30%, about 40%, about 50%, about 60%, about 70%, about 80%, about 90%, or about 95%.

Some embodiments provide a of inhibiting mammalian cell proliferation, comprising contacting the mammalian cell with (a) mithramycin, or a pharmaceutically acceptable salt thereof, and (b) and immunotherapy. Some embodiments provide a of inhibiting mammalian cell proliferation, comprising contacting the mammalian cell with (a) mithramycin, or a pharmaceutically acceptable salt thereof, and (b) and immunotherapy; wherein the amounts of (a) and (b) together are effective in inhibiting mammalian cell proliferation. In some embodiments, the contacting occurs in vivo. In other embodiments, the contacting occurs in vitro. In some embodiments, the mammalian cell is a mammalian cancer cell.

In some embodiments (when the contacting occurs in vivo), the contacting occurs in a subject. In some embodiments, the expression of one or more inflammatory factors in the subject is inhibited. In some embodiments, the expression of the one or more inflammatory factors in the subject is inhibited by about 10% to about 95%, for example, about 10% to about 30%, about 30% to about 50%, about 50% to about 70%, about 70% to about 95%, about 10%, about 20%, about 30%, about 40%, about 50%, about 60%, about 70%, about 80%, about 90%, or about 95%. In some embodiments, the one or more inflammatory factors are selected from CXCL1, MIP3α, MMP2, TPO, E-selectin, Leptin-R, IL-3, and IL-10. In some embodiments, the one or more inflammatory factors are associated with a metastatic colorectal cancer. In some embodiments, the one or more inflammatory factors are independently selected from CXCL1, MIP3α, MMP2, and TPO. In some embodiments, the one or more inflammatory factors are associated with increased tumor cell migration. In some embodiments, the one or more inflammatory factors include E-selectin. In some embodiments, the one or more inflammatory factors are associated with neoangiogenesis. In some embodiments, the one or more inflammatory factors include leptin-R. In some embodiments, the one or more inflammatory factors are selected from IL-3 and IL-10. In some embodiments, the one or more inflammatory factors are independently selected from E-selectin, leptin-R, CXCL1, MIP3α, MMP2, and TPO.

In some embodiments, a reduction in Ki-67 and/or Lgr5 expression occurs in the subject. In some embodiments, the expression is reduced by about 10% to about 95%, for example, about 10% to about 30%, about 30% to about 50%, about 50% to about 70%, about 70% to about 95%, about 10%, about 20%, about 30%, about 40%, about 50%, about 60%, about 70%, about 80%, about 90%, or about 95%. In some embodiments, E-cadherin, IL12 p70, and/or Granzyme B expression is increased in the subject. In some embodiments, the expression is increased by about 10% to about 95%, for example, about 10% to about 30%, about 30% to about 50%, about 50% to about 70%, about 70% to about 95%, about 10%, about 20%, about 30%, about 40%, about 50%, about 60%, about 70%, about 80%, about 90%, or about 95%.

Some embodiments provide a method of reducing the number of cancer initiating stem cells in a population of cells, comprising contacting the population of cells with (a) mithramycin, or a pharmaceutically acceptable salt thereof, and (b) an immunotherapy.

In other embodiments, the contacting occurs in vitro. In some embodiments, the contacting occurs in vivo. In some embodiments, (when the contacting occurs in vivo), the (a) mithramycin, or pharmaceutically acceptable salt thereof, and (b) the immunotherapy are administered to a subject. In some embodiments, the reduction is observed by quantifying the cancer initiating stem cells in a biopsy sample taken from the subject before administration and a biopsy sample taken from the subject after administration (e.g., about 12 hours after administration, about 1 day after administration, about 2 days after administration, about 4 days after administration, about 1 week after administration, about 10 days after administration, about 2 weeks after administration, about 3 weeks after administration, about 4 weeks after administration, about 1 month after administration, or about 2 months after administration), wherein the number of cancer initiating tumor cells observed in the biopsy sample after administration is lower than the number of cancer initiating tumor cells observed in the biopsy sample before administration. In some embodiments, the population of cells is measured by flow cytometry.

In some embodiments, the expression of one or more inflammatory factors in the subject is inhibited. In some embodiments, the expression of the one or more inflammatory factors in the subject is inhibited by about 10% to about 95%, for example, about 10% to about 30%, about 30% to about 50%, about 50% to about 70%, about 70% to about 95%, about 10%, about 20%, about 30%, about 40%, about 50%, about 60%, about 70%, about 80%, about 90%, or about 95%. In some embodiments, the one or more inflammatory factors are selected from CXCL1, MIP3α, MMP2, TPO, E-selectin, Leptin-R, IL-3, and IL-10. In some embodiments, the one or more inflammatory factors are associated with a metastatic colorectal cancer. In some embodiments, the one or more inflammatory factors are independently selected from CXCL1, MIP3α, MMP2, and TPO. In some embodiments, the one or more inflammatory factors are associated with increased tumor cell migration. In some embodiments, the one or more inflammatory factors include E-selectin. In some embodiments, the one or more inflammatory factors are associated with neoangiogenesis. In some embodiments, the one or more inflammatory factors include leptin-R. In some embodiments, the one or more inflammatory factors are selected from IL-3 and IL-10. In some embodiments, the one or more inflammatory factors are independently selected from E-selectin, leptin-R, CXCL1, MIP3α, MMP2, and TPO.

In some embodiments, a reduction in Ki-67 and/or Lgr5 expression occurs in the subject. In some embodiments, the expression is reduced by about 10% to about 95%, for example, about 10% to about 30%, about 30% to about 50%, about 50% to about 70%, about 70% to about 95%, about 10%, about 20%, about 30%, about 40%, about 50%, about 60%, about 70%, about 80%, about 90%, or about 95%. In some embodiments, E-cadherin, IL12 p70, and/or Granzyme B expression is increased in the subject. In some embodiments, the expression is increased by about 10% to about 95%, for example, about 10% to about 30%, about 30% to about 50%, about 50% to about 70%, about 70% to about 95%, about 10%, about 20%, about 30%, about 40%, about 50%, about 60%, about 70%, about 80%, about 90%, or about 95%.

In some embodiments, the population of cells comprises non-cancerous cells. In some embodiments, the non-cancerous cells comprise epithelial cells, muscle cells, connective cells, nerve cells, blood cells, or any combination thereof.

In some embodiments, the reduction in the population of non-cancerous cells is less than the reduction in the population of cancer initiating stem cells. In some embodiments, the reduction in the population of non-cancerous cells is from about 0.1% to about 50% of the reduction in the population of cancer initiating stem cells. For example, from about 0.1% to about 0.5%, from about 0.5% to about 1%, from about 1% to about 5%, from about 5% to about 10%, from about 10% to about 20%, from about 20% to about 30%, from about 30% to about 50%, about 0.1%, about 0.3%, about 0.5%, about 0.8%, about 1%, about 2%, about 5%, about 10%, about 20%, about 30%, about 40%, or about 50%.

Some embodiments provides a method of reducing the size of a tumor in a subject, the method comprising administering (a) mithramycin, or a pharmaceutically acceptable salt thereof, and (b) an immunotherapy, to a subject in need thereof.

Some embodiments provides a method of reducing the size of a tumor in a subject, the method comprising administering (a) mithramycin, or a pharmaceutically acceptable salt thereof, and (b) pembrolizumab, to a subject in need thereof.

Some embodiments provides a method of reducing the size of a tumor in a subject, the method comprising administering (a) mithramycin, or a pharmaceutically acceptable salt thereof, and (b) nivolumab, to a subject in need thereof.

In some embodiments, reducing the size of the tumor in the subject comprises reducing the weight of the tumor. In some embodiments, the weight of the tumor is reduced by about 5% to about 99% (e.g., about 5% to about 25%, about 25% to about 45%, about 45% to about 65%, about 65% to about 85%, about 85% to about 95%, about 75% to about 90%, about 80% to about 85%, about 5%, about 10%, about 15%, about 20%, about 25%, about 30%, about 35%, about 40%, about 45%, about 50%, about 55%, about 60%, about 65%, about 70%, about 75%, about 80%, about 81%, about 82%, about 83%, about 84%, about 85%, about 90%, or about 95%. In some embodiments, the weight of the tumor is reduced by about 80% to about 85%. In some embodiments, reducing the size of the tumor in the subject comprises reducing the volume of the tumor. In some embodiments, the volume of the tumor is reduced by about 5% to about 99% (e.g., about 5% to about 25%, about 25% to about 45%, about 45% to about 65%, about 65% to about 85%, about 85% to about 95%, about 75% to about 90%, about 80% to about 85%, about 5%, about 10%, about 15%, about 20%, about 25%, about 30%, about 35%, about 40%, about 45%, about 50%, about 55%, about 60%, about 65%, about 70%, about 75%, about 80%, about 81%, about 82%, about 83%, about 84%, about 85%, about 90%, or about 95%. In some embodiments, the volume of the tumor is reduced by about 80% to about 85%. In some embodiments, reduction in the size of the tumor is measured by a caliper.

In some embodiments, the tumor is at high risk of metastasizing. In some embodiments, the tumor comprises lung cancer cells or colorectal cancer cells. In some embodiments, the tumor comprises lung cancer cells. In other embodiments, the tumor comprises colorectal cancer cells. In some embodiments, the tumor is an adenocarcinoma, a gastrointestinal carcinoid tumor, a gastrointestinal stromal tumor (GIST), or a sarcoma.

In some embodiments, the metastasis is a central nervous system metastasis. In some embodiments, the immunotherapy comprises an immune checkpoint inhibitor. In some embodiments, the immunotherapy modulates (e.g., inhibits) PD-1 or α-PD-L1. In some embodiments, the immunotherapy comprises an anti-PD-1 and/or an anti-α-PD-L1 monoclonal antibody. In some embodiments, the immunotherapy is selected from alemtuzumab, atezolizuman, avelumab, ipilimumab, ofatumumab, nivolumab, pembrolizumab, cemiplimab, rituximab, and durvalumab. In some embodiments, the immunotherapy is nivolumab or pembrolizumab. In some embodiments, the mithramycin, or a pharmaceutically acceptable salt thereof, is administered orally. In some embodiments, the immunotherapy is administered parenterally. In some embodiments, the mithramycin, or a pharmaceutically acceptable salt thereof, and the immunotherapy are administered at substantially the same time. In some embodiments, the mithramycin, or a pharmaceutically acceptable salt thereof, and the immunotherapy are administered sequentially, in either order. In some embodiments, the mithramycin, or a pharmaceutically acceptable salt thereof, and the immunotherapy are administered on different dosing schedules, as described herein.

In some embodiments, the mithramycin, or a pharmaceutically acceptable salt thereof, is administered at a dose of about 0.5 mg/kg to about 10.0 mg/kg of any value in between; for example, about 0.5 mg/kg to about 1.5 mg/kg, about 1 mg/kg to about 2 mg/kg, about 1.5 mg/kg to about 2.5 mg/kg, about 2 mg/kg to about 3 mg/kg, about 2.5 mg/kg to about 3.5 mg/kg, about 3 mg/kg to about 4 mg/kg, about 3.5 mg/kg to about 4.5 mg/kg, about 4 mg/kg to about 5 mg/kg, about 4.5 mg/kg to about 5.5 mg/kg, about 5 mg/kg to about 6 mg/kg, about 5.5 mg/kg to about 6.5 mg/kg, about 6 mg/kg to about 7 mg/kg, about 6.5 mg/kg to about 7.5 mg/kg, about 7 mg/kg to about 8 mg/kg, about 7.5 mg/kg to about 8.5 mg/kg, about 8 mg/kg to about 9 mg/kg, about 8.5 mg/kg to about 9.5 mg/kg, about 9 mg/kg to about 10 mg/kg, or any value in between.

In some embodiments, the immunotherapy is administered at a standard dose, for example, the dose recommended on a package insert and/or product label, as prescribed by a physician.

In some embodiments, the mithramycin, or a pharmaceutically acceptable salt thereof, is administered daily. In other embodiments, the mithramycin, or a pharmaceutically acceptable salt thereof, is administered every other day. In still other embodiments, the mithramycin, or a pharmaceutically acceptable salt thereof, is administered weekly.

In some embodiments, the immunotherapy is administered daily. In other embodiments, the immunotherapy is administered every other day. In still other embodiments, the immunotherapy is administered weekly. In some embodiments, the immunotherapy is administered in one or more cycles, wherein each cycle comprises administration of the immunotherapy once every three weeks. In some embodiments, the immunotherapy is administered over 3-10 cycles. In other embodiments, the immunotherapy is administered over 3-6 cycles.

In some embodiments, the expression of one or more inflammatory factors in the subject is inhibited. In some embodiments, the expression of the one or more inflammatory factors in the subject is inhibited by about 10% to about 95%, for example, about 10% to about 30%, about 30% to about 50%, about 50% to about 70%, about 70% to about 95%, about 10%, about 20%, about 30%, about 40%, about 50%, about 60%, about 70%, about 80%, about 90%, or about 95%. In some embodiments, the one or more inflammatory factors are selected from CXCL1, MIP3α, MMP2, TPO, E-selectin, Leptin-R, IL-3, and IL-10. In some embodiments, the one or more inflammatory factors are associated with a metastatic colorectal cancer. In some embodiments, the one or more inflammatory factors are independently selected from CXCL1, MIP3α, MMP2, and TPO. In some embodiments, the one or more inflammatory factors are associated with increased tumor cell migration. In some embodiments, the one or more inflammatory factors include E-selectin. In some embodiments, the one or more inflammatory factors are associated with neoangiogenesis. In some embodiments, the one or more inflammatory factors include leptin-R. In some embodiments, the one or more inflammatory factors are selected from IL-3 and IL-10. In some embodiments, the one or more inflammatory factors are independently selected from E-selectin, leptin-R, CXCL1, MIP3α, MMP2, and TPO.

In some embodiments, a reduction in Ki-67 and/or Lgr5 expression occurs in the subject. In some embodiments, the expression is reduced by about 10% to about 95%, for example, about 10% to about 30%, about 30% to about 50%, about 50% to about 70%, about 70% to about 95%, about 10%, about 20%, about 30%, about 40%, about 50%, about 60%, about 70%, about 80%, about 90%, or about 95%. In some embodiments, E-cadherin, IL12 p70, and/or Granzyme B expression is increased in the subject. In some embodiments, the expression is increased by about 10% to about 95%, for example, about 10% to about 30%, about 30% to about 50%, about 50% to about 70%, about 70% to about 95%, about 10%, about 20%, about 30%, about 40%, about 50%, about 60%, about 70%, about 80%, about 90%, or about 95%. Some embodiments provide a pharmaceutical composition comprising mithramycin, or a pharmaceutically acceptable salt thereof, and immunotherapy, and at least on pharmaceutically acceptable excipient. In some embodiments, the composition is formulated for parenteral administration. In some embodiments, wherein the composition is formulated as a solution. In other embodiments, the composition is formulated as a suspension.

In some embodiments, the mithramycin is a pharmaceutically acceptable salt. In other embodiments, the mithramycin is a solvate, for example, a hydrate. In still other embodiments, the mithramycin is a pharmaceutically acceptable salt of a solvate. In some embodiments, the mithramycin is a complex, for example, with or more metal ions.

As used herein, "mithramycin" refers to an antineoplastic antibiotic produced by *Streptomyces plicatus*. Also known as plicamycin, one skilled in the art would understand that mithramycin includes several structurally related compounds, each with a chromomycin core, but possessing different stereochemistry on the glycosyl side chains. This entire group of structures is envisioned as being included in the term mithramycin.

As used herein, terms "treat" or "treatment" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable. "Treatment" can also mean prolonging survival as compared to expected survival if not receiving treatment.

As used herein, the term "subject," refers to any animal, including mammals such as mice, rats, other rodents, rabbits, dogs, cats, swine, cattle, sheep, horses, primates, and humans. In some embodiments, the subject is a human. In some embodiments, the subject has experienced and/or exhibited at least one symptom of cancer. In some embodiments, the subject has been identified or diagnosed as having a cancer (e.g., as determined using a regulatory agency-approved, e.g., FDA-approved, assay or kit). The subject can be a subject with a tumor(s) that are at high risk for metastasis (e.g., identified as positive using a regulatory agency-approved, e.g., FDA-approved, assay or kit). In some embodiments, the subject is suspected of having cancer.

The term "regulatory agency" refers to a country's agency for the approval of the medical use of pharmaceutical agents with the country. For example, a non-limiting example of a regulatory agency is the U.S. Food and Drug Administration (FDA).

In some embodiments of any of the methods or uses described herein, the cancer is a hematological cancer. In some embodiments of any of the methods or uses described herein, the cancer is a solid tumor. In some embodiments of any of the methods or uses described herein, the cancer is a lung cancer (e.g., small cell lung carcinoma or non-small cell lung carcinoma), testicular cancer, breast cancer, mammary cancer, colorectal cancer (e.g., metastatic colorectal cancer), papillary renal cell carcinoma, or cervical cancer.

In some embodiments of any of the methods or uses described herein, the cancer is selected from the group of: acute lymphoblastic leukemia (ALL), acute myeloid leukemia (AML), cancer in adolescents, adrenocortical carcinoma, anal cancer, appendix cancer, astrocytoma, atypical teratoid/rhabdoid tumor, basal cell carcinoma, bile duct cancer, bladder cancer, bone cancer, brain stem glioma, brain tumor, breast cancer, bronchial tumor, Burkitt lymphoma, carcinoid tumor, unknown primary carcinoma, cardiac tumors, cervical cancer, childhood cancers, chordoma, chronic lymphocytic leukemia (CLL), chronic myelogenous leukemia (CML), chronic myeloproliferative neoplasms, neoplasms by site, neoplasms, colon cancer, colorectal cancer, craniopharyngioma, cutaneous T-cell lymphoma, cutaneous angiosarcoma, bile duct cancer, ductal carcinoma in situ, embryonal tumors, endometrial cancer, ependymoma, esophageal cancer, esthesioneuroblastoma, Ewing sarcoma, extracranial germ cell tumor, extragonadal germ cell tumor, extrahepatic bile duct cancer, eye cancer, fallopian tube cancer, fibrous histiocytoma of bone, gallbladder cancer, gastric cancer, gastrointestinal carcinoid tumor, gastrointestinal stromal tumors (GIST), germ cell tumor, gestational trophoblastic disease, glioma, hairy cell tumor, hairy cell leukemia, head and neck cancer, thoracic neoplasms, head and neck neoplasms, CNS tumor, primary CNS tumor, heart cancer, hepatocellular cancer, histiocytosis, Hodgkin's lymphoma, hypopharyngeal cancer, intraocular melanoma, islet cell tumors, pancreatic neuroendocrine tumors, Kaposi sarcoma, kidney cancer, Langerhans cell histiocytosis, laryngeal cancer, leukemia, lip and oral cavity cancer, liver cancer, lung cancer, lymphoma, macroglobulinemia, malignant fibrous histiocytoma of bone, osteocarcinoma, melanoma, Merkel cell carcinoma, mesothelioma, metastatic squamous neck cancer, midline tract carcinoma, mouth cancer, multiple endocrine neoplasia syndromes, multiple myeloma, myelogenous leukemia, myeloid leukemia, multiple myeloma, myeloproliferative neoplasms, nasal cavity and paranasal sinus cancer, nasopharyngeal cancer, neuroblastoma, non-Hodgkin's lymphoma, non-small cell lung cancer, lung neoplasm, pulmonary cancer, pulmonary neoplasms, respiratory tract neoplasms, bronchogenic carcinoma, bronchial neoplasms, oral cancer, oral cavity cancer, lip cancer, oropharyngeal cancer, osteosarcoma, ovarian cancer, pancreatic cancer, papillomatosis, paraganglioma, paranasal sinus and nasal cavity cancer, parathyroid cancer, penile cancer, pharyngeal cancer, pheochromosytoma, pituitary cancer, plasma cell neoplasm, pleuropulmonary blastoma, pregnancy-associated breast cancer, primary central nervous system lymphoma, primary peritoneal cancer, prostate cancer, rectal cancer, colon cancer, colonic neoplasms, renal cell cancer, retinoblastoma, rhabdomyosarcoma, salivary gland cancer, sarcoma, Sezary syndrome, skin cancer, Spitz tumors, small cell lung cancer, small intestine cancer, soft tissue sarcoma, squamous cell carcinoma, squamous neck cancer, stomach cancer, T-cell lymphoma, testicular cancer, throat cancer, thymoma and thymic carcinoma, thyroid cancer, transitional cell cancer of the renal pelvis and ureter, unknown primary carcinoma, urethral cancer, uterine cancer, uterine sarcoma, vaginal cancer, vulvar cancer, and Wilms' tumor.

In some embodiments, a hematological cancer is selected from the group consisting of leukemias, lymphomas (non-Hodgkin's lymphoma), Hodgkin's disease (also called Hodgkin's lymphoma), and myeloma, for instance, acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma (MM). Additional examples of hematological cancers include myeloproliferative disorders (MPD) such as polycythemia vera (PV), essential thrombocytopenia (ET) and idiopathic primary myelofibrosis (IMF/IPF/PMF).

In some embodiments, the cancer is a solid tumor. Examples of solid tumors include, for example colorectal cancer (CRC). In some embodiments, the subject is human.

Although the genetic basis of tumorigenesis may vary between different cancer types, the cellular and molecular mechanisms required for metastasis appear to be similar for all solid tumor types. During a metastatic cascade, the cancer cells lose growth inhibitory responses, undergo alterations in adhesiveness and produce enzymes that can degrade extracellular matrix components. This leads to detachment of tumor cells from the original tumor, infiltration into the circulation through newly formed vasculature, migration and extravasation of the tumor cells at favorable distant sites where they may form colonies.

Accordingly, also provided herein are methods of inhibiting, preventing, aiding in the prevention, or decreasing the symptoms of metastasis of a cancer in a subject in need thereof, the method comprising administering to the subject immunotherapy and mithramycin or a pharmaceutically acceptable salt thereof. Such methods can be used in the treatment of one or more of the cancers described herein. See, e.g., US Publication No. 2013/0029925; International Publication No. WO 2014/083567; and U.S. Pat. No. 8,568,998. See also, e.g., Hezam K et al., Rev Neurosci 2018 Jan. 26; 29:93-98; Gao L, et al., Pancreas 2015 January; 44:134-143; Ding K et al., J Biol Chem 2014 Jun. 6; 289:16057-71; and Amit M et al., Oncogene 2017 Jun. 8; 36:3232-3239. In some embodiments, the cancer is a colorectal cancer. In some embodiments, the metastasis are central nervous system metastasis (e.g., brain metastasis).

The term "metastasis" is an art known term and means the formation of an additional tumor (e.g., a solid tumor) at a site distant from a primary tumor in a subject or subject, where the additional tumor includes the same or similar cancer cells as the primary tumor.

Also provided are methods of decreasing the risk of developing a metastasis or an additional metastasis in a subject having cancer that include: selecting, identifying, or diagnosing a subject as having a cancer at high risk of developing metastasis, and administering mithramycin and immunotherapy to the subject selected, identified, or diagnosed as having a cancer at high risk of developing metastasis. Also provided are methods of decreasing the risk of developing a metastasis or an additional metastasis in a subject having a cancer at high risk of developing metastasis that includes administering mithramycin and immunotherapy to the subject. The decrease in the risk of developing a metastasis or an additional metastasis in subject having a cancer at high risk of developing metastasis can be compared to the risk of developing a metastasis or an additional metastasis in the subject prior to treatment, or as compared to a subject or a population of subjects having a similar or the same subject having a cancer at high risk of developing metastasis that has received no treatment or a different treatment. In some embodiments, the cancer is a colorectal cancer. In some embodiments, the metastasis are central nervous system metastasis (e.g., brain metastasis).

The phrase "risk of developing a metastasis" means the risk that a subject having a primary tumor will develop an additional tumor (e.g., a solid tumor) at a site distant from a primary tumor in a subject over a set period of time, where the additional tumor includes the same or similar cancer cells as the primary tumor. Methods for reducing the risk of developing a metastasis in a subject or subject having a cancer are described herein. In some embodiments, the metastasis are central nervous system metastasis (e.g., brain metastasis).

The phrase "risk of developing additional metastases" means the risk that a subject having a primary tumor and one or more additional tumors at sites distant from the primary tumor (where the one or more additional tumors include the same or similar cancer cells as the primary tumor) will develop one or more further tumors distant from the primary tumor, where the further tumors include the same or similar cancer cells as the primary tumor. Methods for reducing the risk of developing additional metastasis are described herein. In some embodiments, the metastasis are central nervous system metastasis (e.g., brain metastasis).

Also provided is a method for inhibiting cell proliferation, comprising contacting the cell with mithramycin, or a pharmaceutically acceptable salt thereof, and immunotherapy. In some embodiments, the contacting is in vitro. In some embodiments, the contacting is in vivo. In some embodiments, the contacting is in vivo, wherein the method comprises administering mithramycin, or a pharmaceutically acceptable salt thereof, and immunotherapy, to a mammal having a cell having dyregulated cell proliferation. In some embodiments, the mammalian cell is a mammalian cancer cell. In some embodiments, the mammalian cancer cell is any cancer as described herein. In some embodiments, the mammalian cell is a gastrointestinal cell.

As used herein, the term "contacting" refers to the bringing together of indicated moieties in an in vitro system or an in vivo system. For example, "contacting" a cell as described herein includes the administration of mithramycin, or a pharmaceutically acceptable salt thereof, and immunotherapy, provided herein to a subject, such as a human, as well as, for example, introducing mithramycin, or a pharmaceutically acceptable salt thereof, and immunotherapy, into a sample containing a cellular or purified preparation.

Also provided herein is a method of inhibiting cell proliferation, in vitro or in vivo, the method comprising contacting a cell with mithramycin, or a pharmaceutically acceptable salt thereof, and immunotherapy.

The phrase "effective amount" means an amount of compound that, when administered to a subject in need of such treatment, is sufficient to (i) treat a cancer, (ii) attenuate, ameliorate, or eliminate one or more symptoms of the cancer, or (iii) delay the onset of one or more symptoms of the cancer described herein. The amount of mithramycin, or a pharmaceutically acceptable salt thereof, and the amount of an immunotherapy, that will correspond to such an amount will vary depending upon factors such as the particular immunotherapy, the cancer and its severity, the identity (e.g., weight) of the subject in need of treatment, but can nevertheless be routinely determined by one skilled in the art. In some embodiments, the amount of mithramycin, or a pharmaceutically acceptable salt thereof, and the amount of an immunotherapy, together provide an effective amount.

When employed as pharmaceuticals, the combinations described herein (e.g., mithramycin, or a pharmaceutically acceptable salt thereof, and immunotherapy) can be administered in the form of pharmaceutical compositions. Each component of the combination can be prepared as a composition in a manner well known in the pharmaceutical art, and can be administered by a variety of routes, depending upon whether local or systemic treatment is desired and upon the area to be treated.

Administration of the mithramycin, or a pharmaceutically acceptable salt thereof, can be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Oral administration can include a dosage form formulated for once-daily or twice-daily (BID) administration. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or can be, for example, by a continuous perfusion pump. Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like may be necessary or desirable.

Administration of the immunotherapy can be parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or can be, for example, by a continuous perfusion pump.

Also provided herein are pharmaceutical compositions which contain, as the active ingredients mithramycin, or a pharmaceutically acceptable salt thereof, and immunotherapy, with one or more pharmaceutically acceptable carriers (excipients). In some embodiments, the composition is suitable for parenteral administration. In making the compositions provided herein, the active ingredient is typically mixed with an excipient, diluted by an excipient or enclosed within such a carrier in the form of, for example, a solution, a suspension, an emulsion, a pre-filled syringe, or other container. When the excipient serves as a diluent, it can be a solid, semi-solid, or liquid material, which acts as a vehicle, carrier or medium for the active ingredient. Thus, the compositions can be in the form of elixirs, suspensions, emulsions, and solutions.

Suitable pharmaceutically acceptable carriers are well known in the art. Descriptions of some of these pharmaceutically acceptable carriers can be found in The Handbook of Pharmaceutical Excipients, published by the American Pharmaceutical Association and the Pharmaceutical Society of Great Britain.

Methods of formulating pharmaceutical compositions have been described in numerous publications such as Pharmaceutical Dosage Forms: Tablets, Second Edition, Revised and Expanded, Volumes 1-3, edited by Lieberman et al; Pharmaceutical Dosage Forms: Parenteral Medications, Volumes 1-2, edited by Avis et al; and Pharmaceutical Dosage Forms: Disperse Systems, Volumes 1-2, edited by Lieberman et al; published by Marcel Dekker, Inc.

In preparing the compositions in oral dosage form, any of the usual pharmaceutical media can be employed. Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Solid oral preparations can also be coated with substances such as sugars or be enteric-coated so as to modulate major site of absorption. For parenteral administration, the carrier will usually consist of sterile water and other ingredients can be added to increase solubility or preservation. Injectable suspensions or solutions can also be prepared utilizing aqueous carriers along with appropriate additives. The pharmaceutical compositions herein will contain, per dosage unit, e.g., tablet, capsule, powder, injection, teaspoonful and the like, an amount of the active ingredient necessary to deliver an effective dose as described herein.

In some embodiments, about 0.5 mg to about 10 mg of mithramycin, or a pharmaceutically acceptable salt thereof, is administered, for example, about 0.5 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, or about 10 mg.

One skilled in the art will recognize that both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy subjects and/or those suffering from a given disorder, can be completed according to methods well known in the clinical and medical arts.

Provided herein are pharmaceutical kits useful, for example, in the treatment of cancer, which include two or more containers containing (a) a pharmaceutical composition comprising mithramycin, or a pharmaceutically acceptable salt thereof; and (b) an immunotherapy. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

A number of embodiments of the invention have been described. Nevertheless, it will be understood that various modifications may be made without departing from the spirit and scope of the invention. Accordingly, other embodiments are within the scope of the following claims.

EXAMPLES

The following examples illustrate the subject matter described in the present application.

Example 1

Tumoroids show increased expression of sternness factors: 3D nanofiber scaffold-based tumoroid culture for many cancers have been developed.[9-11] Tumoroids are culturable for weeks (tested up to 3 weeks), can be grown up to 500 μm in diameter and exhibit EMT and show chemo drug responses similar to in vivo tumors[9, 10]. Characteristics of tumoroids derived from HT-29 human colon cancer cells are shown in FIG. 1A-1D. FIG. 1A depicts a scaffold matrix held by forceps tip. FIG. 1B depicts scanning electron microscope image (EM) of Day 4 HT-29 tumoroid on the scaffold. FIG. 1C depicts Nuc Blue-stained HT-29 tumoroids in culture. FIG. 1D depicts HT-29 tumoroids that developed features of EMT (decreased E-cadherin and increased α-smooth muscle actin (SMA)) shown by immunofluorescence (IF) staining after 6 days of culture. Tumoroids from breast cancers expand CSCs[11], however, CSC expansion of CRC tumoroids is hitherto unknown. To demonstrate this, two human colon cancer cells were cultured with varying driver mutations, HT29 (p53 mutant, K-RAS wild type, microsatellite stable (MSS)), HCT116 (p53 wild-type, K-RAS mutant, microsatellite instable (MSI)) and CT-26 murine cancer cells (p53 wild-type, K-RAS mutant, MSS)[25] on 3D scaffold for 6 days and examined tumoroids for stemness markers by qPCR and flow cytometry. HT-29 tumoroids showed 50- and 60-fold higher expression of transcription factors NANOG and OCT4, respectively, compared to cells derived from normal colon, CCD841, and 5- and 7-fold compared to monolayer cells (FIG. 1E). Also, HT-29 tumoroids showed a 12- and 5-fold increase in transcription of LGR5 (leucine-rich repeat-containing G-protein coupled receptor) and stem cell related transcription factor (SOX2), respectively, compared to monolayer (FIG. 1F). Further, tumoroids derived from CT-26 cells exhibited a gradual increase in expression of Lgr5 and Sox2 transcripts, as the tumoroids were successively passaged from P1 to P3 (FIG. 1G) on the scaffold. In addition, tumoroids derived from HCT116 cells showed a 5-fold increase in ALDH activity, which is a hallmark of stemness measurable by the aldefluor assay, over monolayer cells (12.5%) (FIG. 1H). These studies suggest that the scaffold induces increased expression of CSC markers and transcription factors both in human and mouse colon cancer cells. Baseline fluorescence was calculated using DEAB. *$p \leq 0.05$; $p \leq 0.01$; *$p \leq 0.001$.

Example 2

Figure 2A:
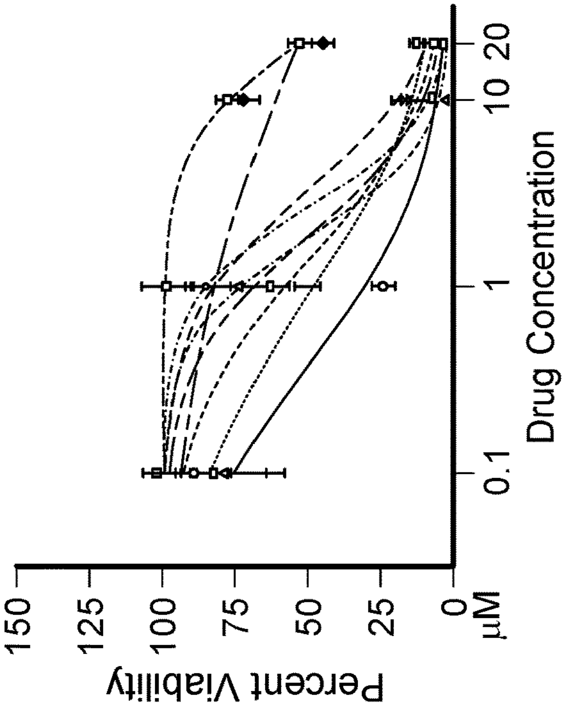
FIG. 2A depicts a plot of percent viability of HT-29 tumoroids after treatment with increasing concentrations of various drugs for 48 hours.
Figure 2B:
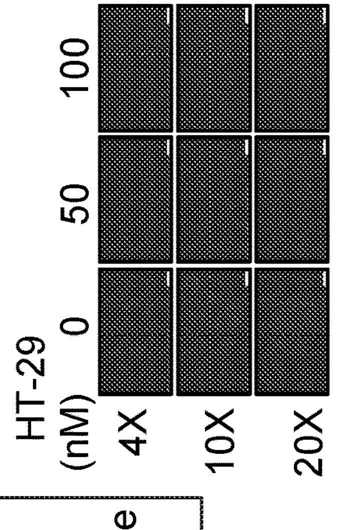
FIG. 2B depicts images of HT29 cells cultured and treated with Mit-A for 48 hrs and stained with Nuc-blue. Scale bar represents 200 μm, 100 μm and 50 μm for 4×, 10× and 20× magnifications, respectively.
Figure 2C:
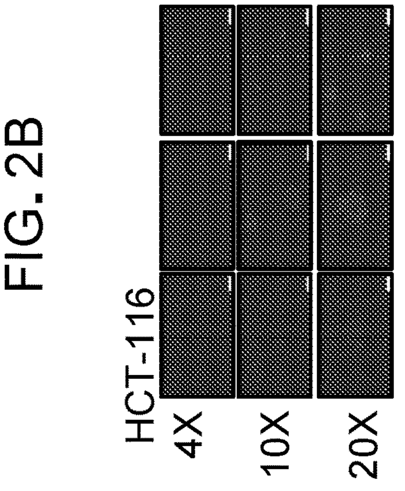
FIG. 2C depicts images of HCT116 cells cultured and treated with Mit-A for 48 hrs and stained with Nuc-blue. Scale bar represents 200 μm, 100 μm and 50 μm for 4×, 10× and 20× magnifications, respectively.
Figure 2D:
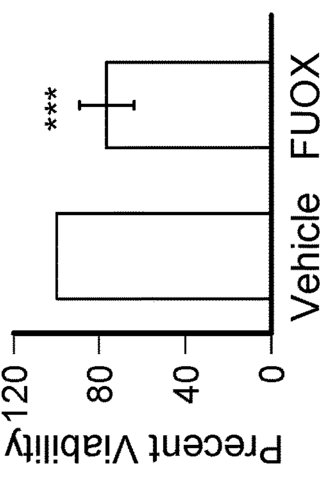
FIG. 2D depicts a bar graph of percent viability of day 4 HT-29 tumoroids after treatment with vehicle or FUOX.
Figure 2D:

NCI diversity library screening for the discovery of anti-CSC targets: An NCI Oncology Drugs set of FDA-approved drugs was screened using tumoroid platform in HT29 cells. The top nine drugs were selected as candidate CSC inhibitors and assayed their ability to decrease viability of CRC CSCs using HT29 tumoroids. The tumoroids were treated for 48 hours with different drug candidates including cisplatin. Of these, Mit-A was found to have the lowest $IC_{50}$ of all drugs tested (in the nanomolar range) (FIG. 2A). Thus, Mit-A was considered to be the most effective against HT29 cells. Mit-A, an antineoplastic antibiotic[26], has been used in the treatment of testicular cancer', chronic myeloid leukemia[27], and as a metastasis inhibitor[28]. Moreover, Mit-A treatment inhibited the growth of HT-29 and HCT-116 tumoroids (FIG. 2B-C) cultured as in the experiment used to generate the FIG. 2A data. Both the number and size of tumoroids were decreased in a dose-dependent manner. However, only 20% growth inhibition was observed when HT29 tumoroids were treated with a mixture of chemotherapy, such as 25 μM of 5-FU and 0.625 μM of oxaliplatin (FUOX) (FIG. 2D), which is being used as a standard of care for CRCs. Cell viability was assessed on day 6 by CellTiter-Glo assay (FIGS. 2A and 2D).

Example 3

Figures 3A, 3B, 3C, 3D, 3E, 3F:
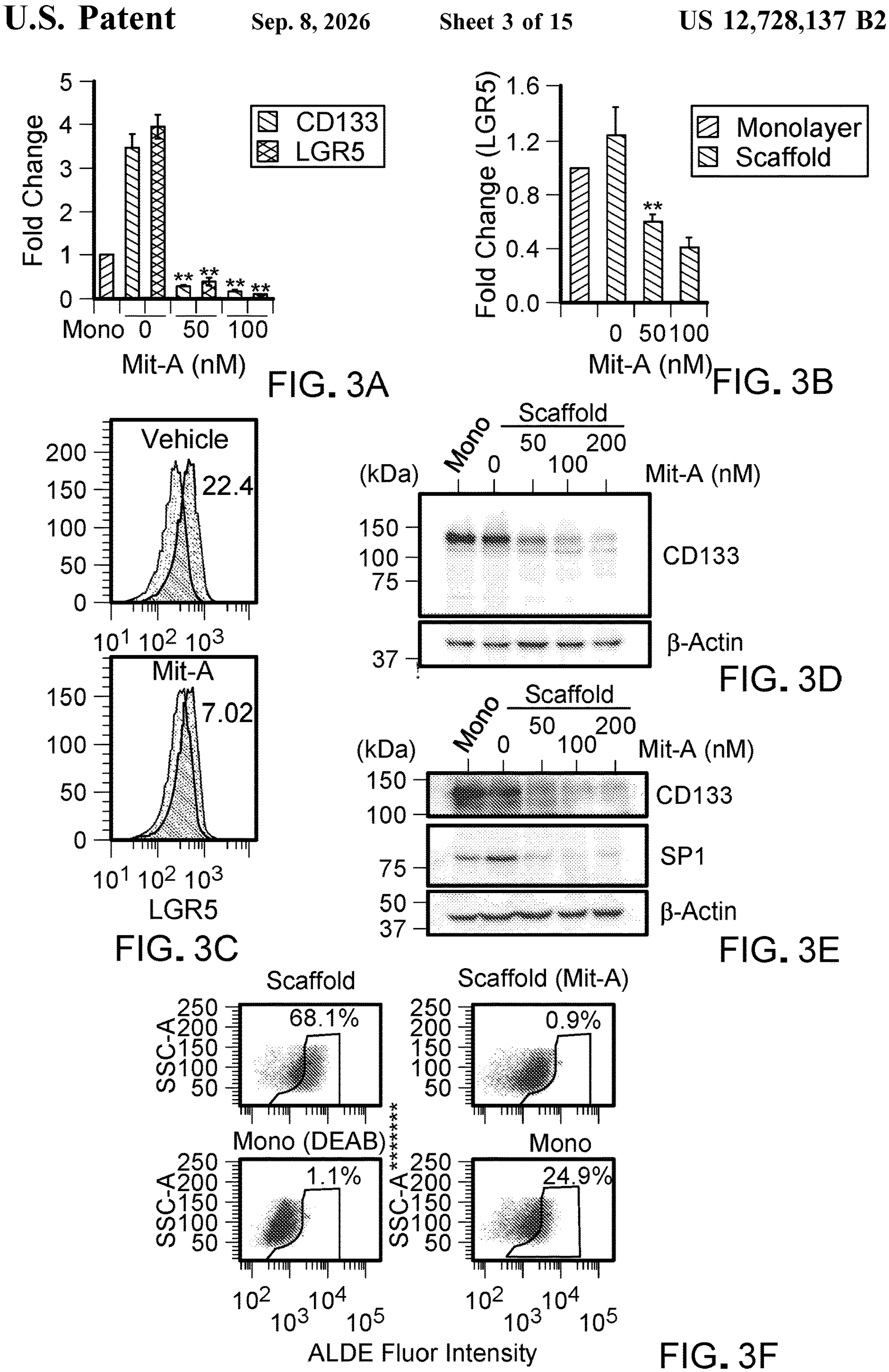
FIG. 3A depicts a qPCR bar graph of CD133 and LGR5 gene expression in monolayer vs. 3D scaffold cultures of HT29.
FIG. 3B depicts a qPCR bar graph of CD133 and LGR5 gene expression in monolayer vs. 3D scaffold cultures of HCT116.
FIG. 3C depicts LGR-5 expression in HCT-116 tumoroids exposed to Mit-A (100 nM) for 48 hrs quantified by flow cytometry.
FIG. 3D depicts expression of CD133 and Sp1 in HT29 as assessed by Western blotting.
FIG. 3E depicts expression of CD133 and Sp1 in HCT116 as assessed by Western blotting.
FIG. 3F depicts ALDH activity in HT-29 cells cultured on scaffold in the presence of Mit-A (100 nM) as assessed by flow cytometry.

Mit-A inhibits CSC expansion in CRC tumoroids: To determine whether Mit-induced reduction in tumoroid growth is due to changes in stemness, the expression of stemness markers was analyzed by qPCR, flow cytometry and/or Western blotting. Cells were cultured on scaffold and examined on day 6. Both HT-29 and HCT-116 tumoroids showed a decrease in stemness factors when treated with Mit-A. Mit-A inhibited CD133 (FIG. 3A, B, D, E) in a dose-dependent manner and LGR5 expression, which decreased from 22.4% to 7.02% (FIG. 3C). In addition, Mit-A treatment reduced expression of Sp1 (FIG. 3E), a stemness-related transcription factor[29]. Lastly, flow cytometry analysis demonstrated that HT29 tumoroids showed a 2.5-fold increase in ALDH activity over monolayer, and Mit-A treatment significantly inhibited ALDH activity (decreased from 68.1% to 0.9% in tumoroids) (FIG. 3F). These data clearly indicate that Mit-A can inhibit tumoroid growth in part by suppressing the stemness marker expression in CRCs. These results demonstrate that the role of Mit-A as an anti-CSC therapeutic in combination CIx. **$p \leq 0.01$.

Example 4

Figures 4A, 4B, 4C, 4D, 4E, 4F, 4G:
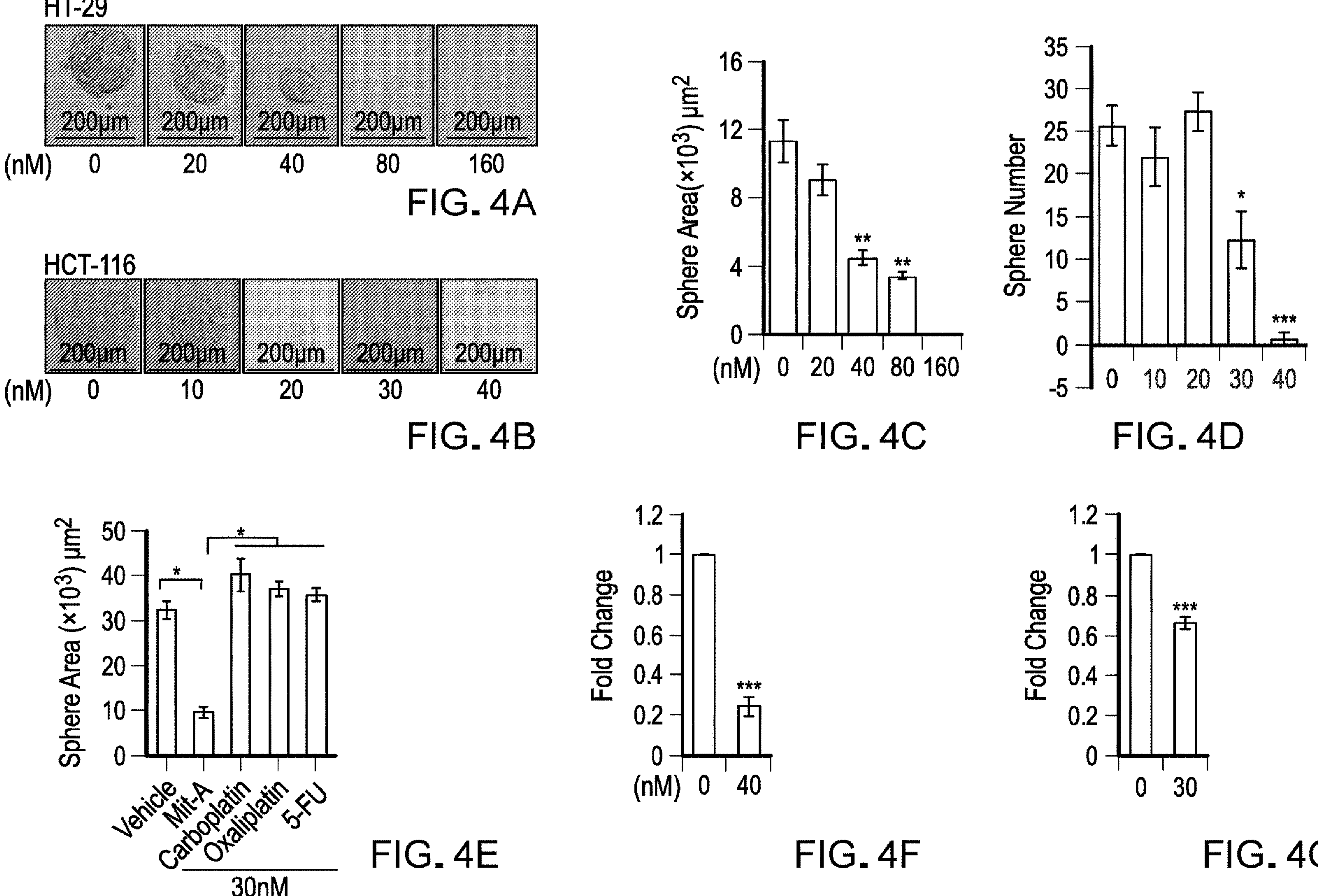
FIG. 4A depicts inverted microscope images of HT29 cells plated in a 96 well ultra-low attachment plate in the presence of indicated doses of Mit-A.
FIG. 4B depicts inverted microscope images of HCT116 cells plated in a 96 well ultra-low attachment plate in the presence of indicated doses of Mit-A.
FIG. 4C depicts a bar graph of area of spheres counted using Image J software.
FIG. 4D depicts a bar graph of area of spheres counted using Image J software.
FIG. 4E depicts a bar graph of area of the spheres treated with different anti-cancer drugs or Mit-A.
FIG. 4F depicts OCT-4 gene expression in HT29 spheres treated with vehicle or Mit-A.
FIG. 4G depicts OCT-4 gene expression in HCT116 spheres treated with vehicle or Mit-A.

Mit-A can suppress cancer sternness in spheres: HT-29 and HCT-116 colon cancer cells grown in sphere forming media in low attachment conditions for 5 days. In all cell lines, Mit-A significantly reduced the overall size (sphere area) (FIGS. 4A-C and E) and the number of the spheres (FIG. 4D) in a dose-dependent manner. Also, Mit-A is more potent in inhibiting sphere growth vs. the standard of care drugs carboplatin, oxaliplatin, and 5-fluorouracil (5-FU) (FIG. 4E). Moreover, Mit-A inhibited the colonosphere formation (self-renewal properties of CRC CSCs) through the inhibition of stem cell related transcription factor, OCT4 (FIGS. 4F and G). Each data point indicates mean±SEM. *$p \leq 0.05$; $p \leq 0.01$; *$p \leq 0.001$.

Example 5

Figures 5A, 5B, 5C:
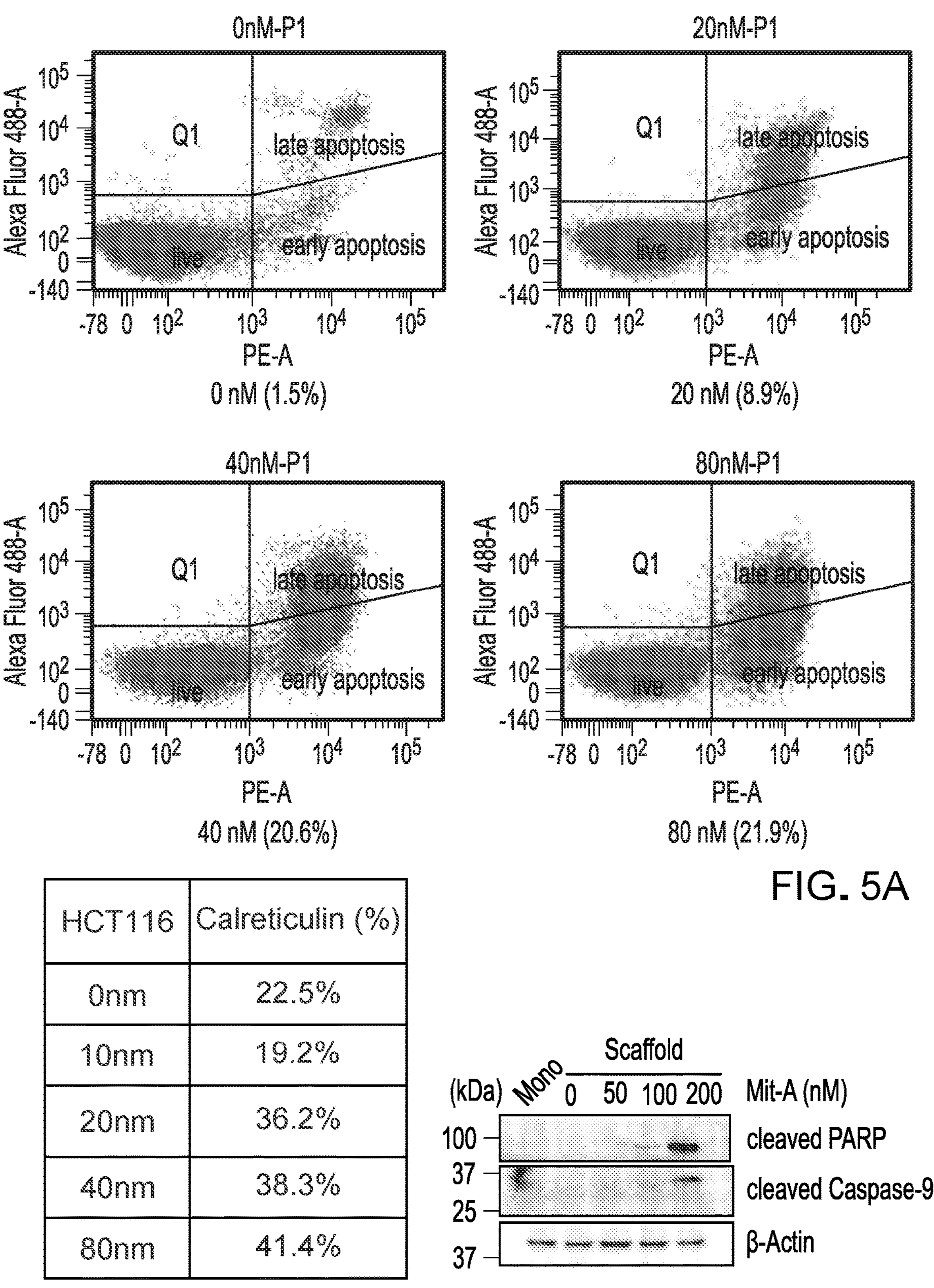
FIG. 5A depicts HCT116 cells grown on monolayer after treatment with Mit-A for 48 hours and analyzed by flow-cytometry.
FIG. 5B is a table showing results of flow cytometry analysis of cells stained with rabbit anti-Calreticulin antibody followed by goat anti-rabbit secondary antibody.
FIG. 5C depicts a Western blot of proteins isolated from cells thats were grown on scaffolds for four days and treated with Mit-A for 48 hours at indicated doses.
Figure 5D:
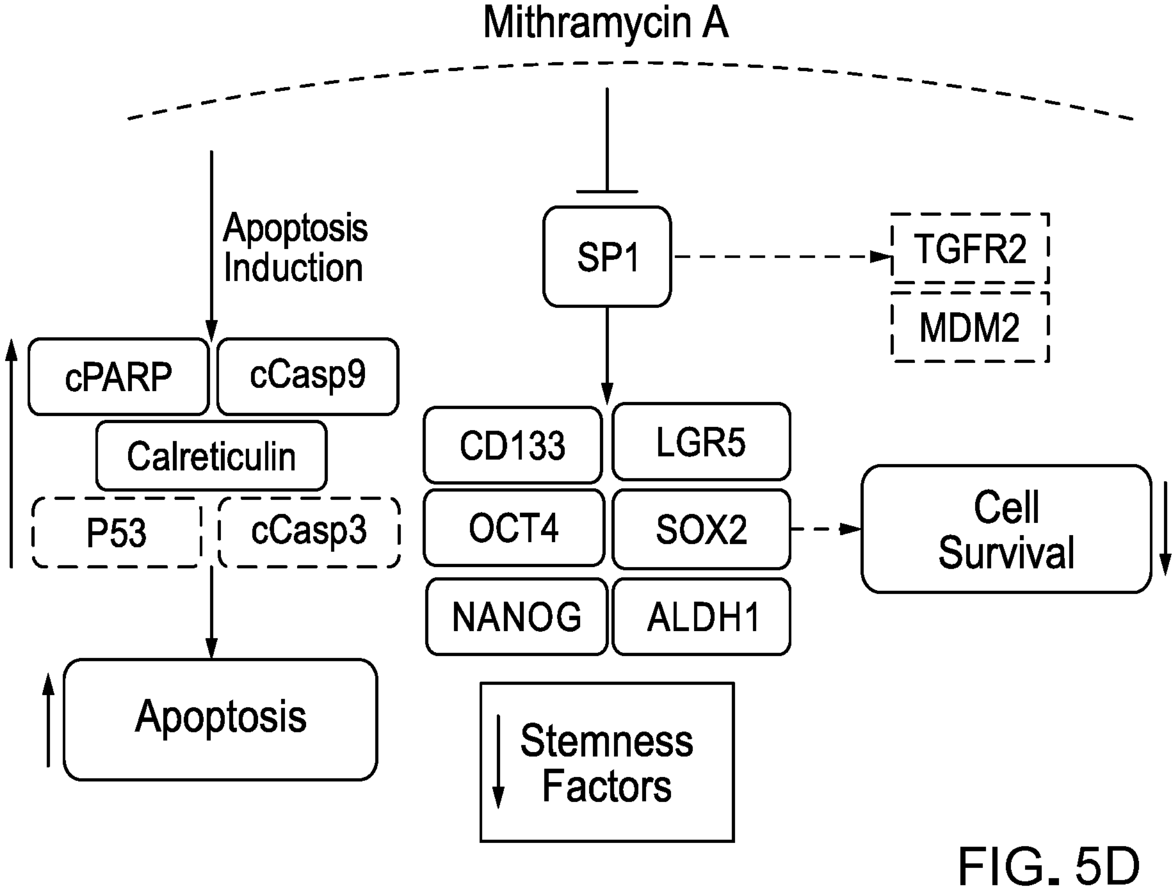
FIG. 5D depicts a proposed model of Mit-A action.
Figure 10:
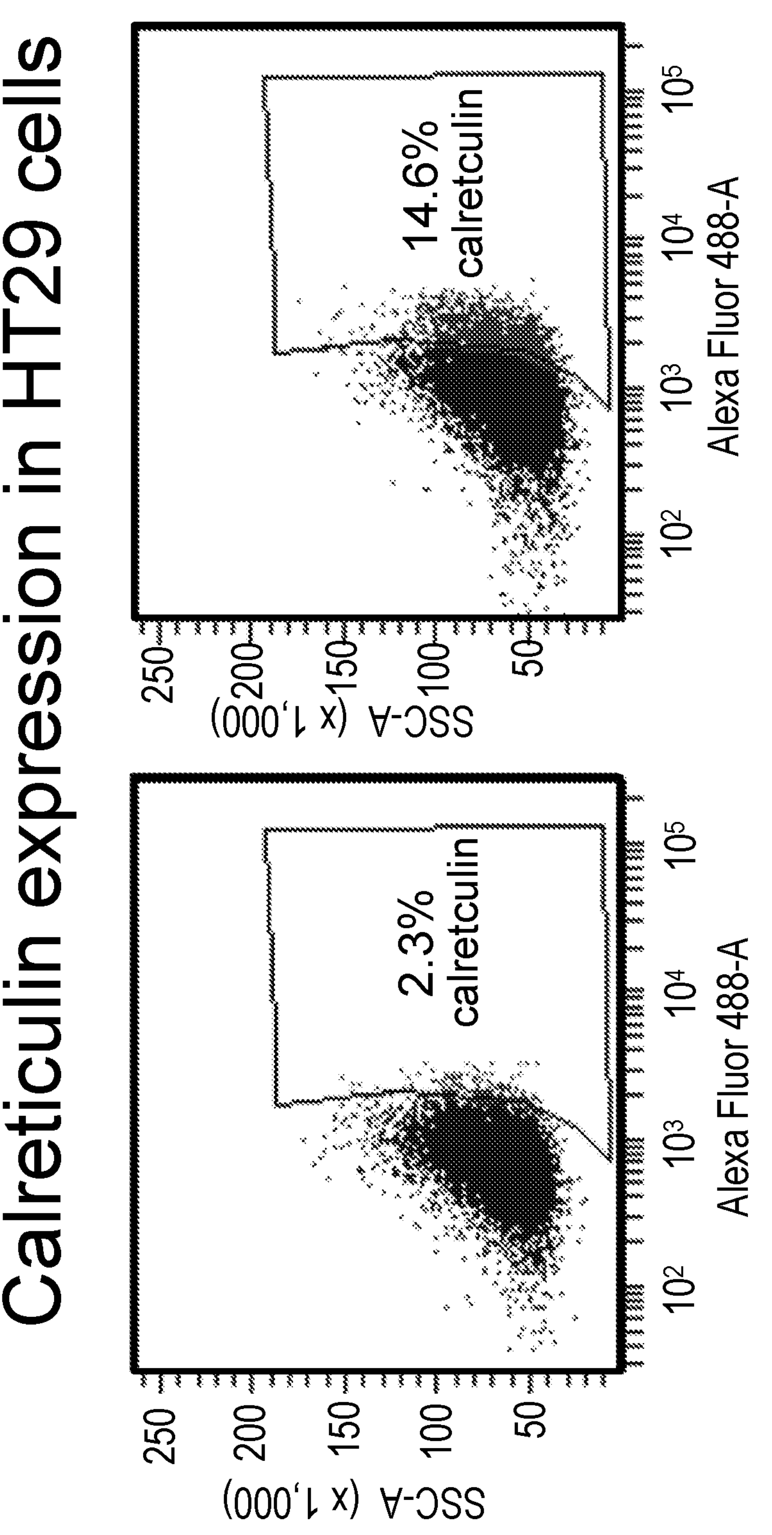
FIG. 10 depicts HT-29 cells grown on monolayer after treatment with 50 nM Mit-A for 48 hours and analyzed by flow-cytometry (vehicle vs. Mit-A).

Mit-A induces immunogenic cancer cell death (ICD): ICD is a form of cell death whereas cells die through a necrotic pathway and release damage associated molecular pattern molecules (DAMPs)[30]. FIG. 5A depicts HCT116 cells grown on monolayer after treatment with Mit-A for 48 hours and analyzed by flow-cytometry. FIG. 10 depicts HT-29 cells grown on monolayer after treatment with 50 nM Mit-A for 48 hours and analyzed by flow-cytometry. The percentage of necrotic cell death (Annexin V+ and Sytox Green+) with different concentration of Mit-A is shown. Mit-A treatment induced a significant dose-dependent increase (1.5% in control vs. 22% in response to 80 nM Mit-A) in necrotic cell death in HCT116 and HT29. Increase in cell death correlated with an increase in the cell surface expression of calreticulin in Mit-A treated HCT116 cells (FIG. 5B). In addition, Mit-A induced PARP1 and caspase-9 mediated mitochondrial cell death in CRCs (FIG. 5C), suggesting activation of mitochondrial cell death in these cells. This evidence demonstrates that Mit-A induces apoptosis through ICD pathway and inhibits the growth of CRC CSCs through the inhibition of transcription factors and stem cell markers including but not limited to SP1, CD133, LGR5 and OCT4 (FIG. 5D).

Example 6

Figures 6A, 6B, 6C, 6D, 6E:
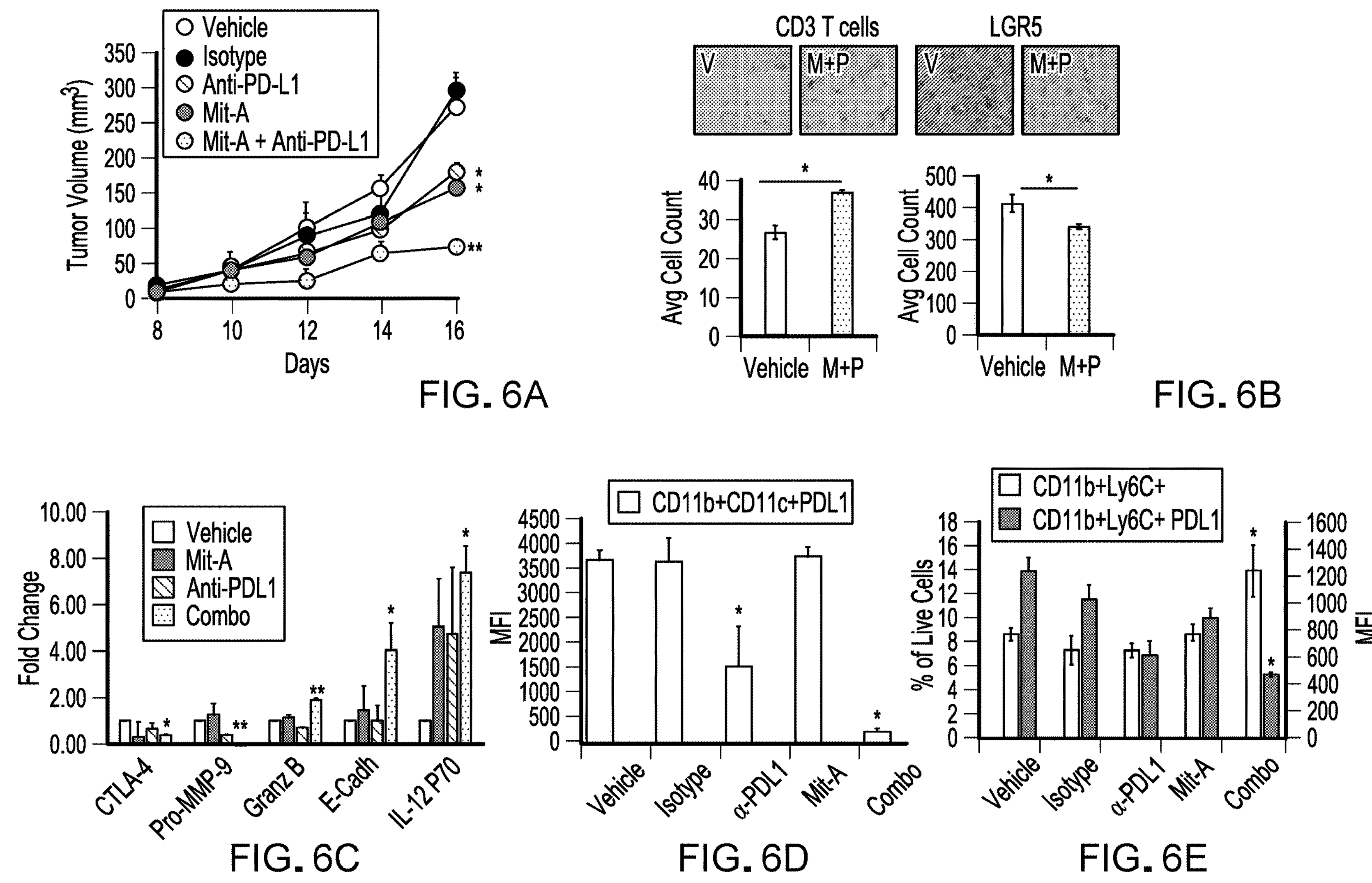
FIG. 6A depicts a plot tumor volume measured on indicated days using a caliper after various treatments.
FIG. 6B depicts immunohistochemistry (IHC) of a representative section from vehicle and Mit-A+anti-PDL1 (M+P) treated tumors. Bar graphs represent average (5 fields/tumor section; n=2) number±SD of cells stained for T cells (using anti-CD3) or LGR5.
FIG. 6C depicts a semiquantitative assessment of mouse cytokines in tumor lysates of control, αPD-L1, Mit-A or combination (M+P) (n=2) using mouse cytokine array C1 (RayBiotech).
FIG. 6D depicts a bar graph of the mean fluorescent intensity (MFI) of PD-L1 staining in DCs ($CD11b^+CD11c^+$) isolated from spleen (n=4).
FIG. 6E depicts a bar graph of the mean fluorescent intensity (MFI) of PD-L1 staining in splenocytes expressing $CD11b^+Ly6C^{high}$ (m-MDSCs) (blue) and MFI of PD-L1 staining in m-MDSCs (orange) (n=4).
Figure 11:
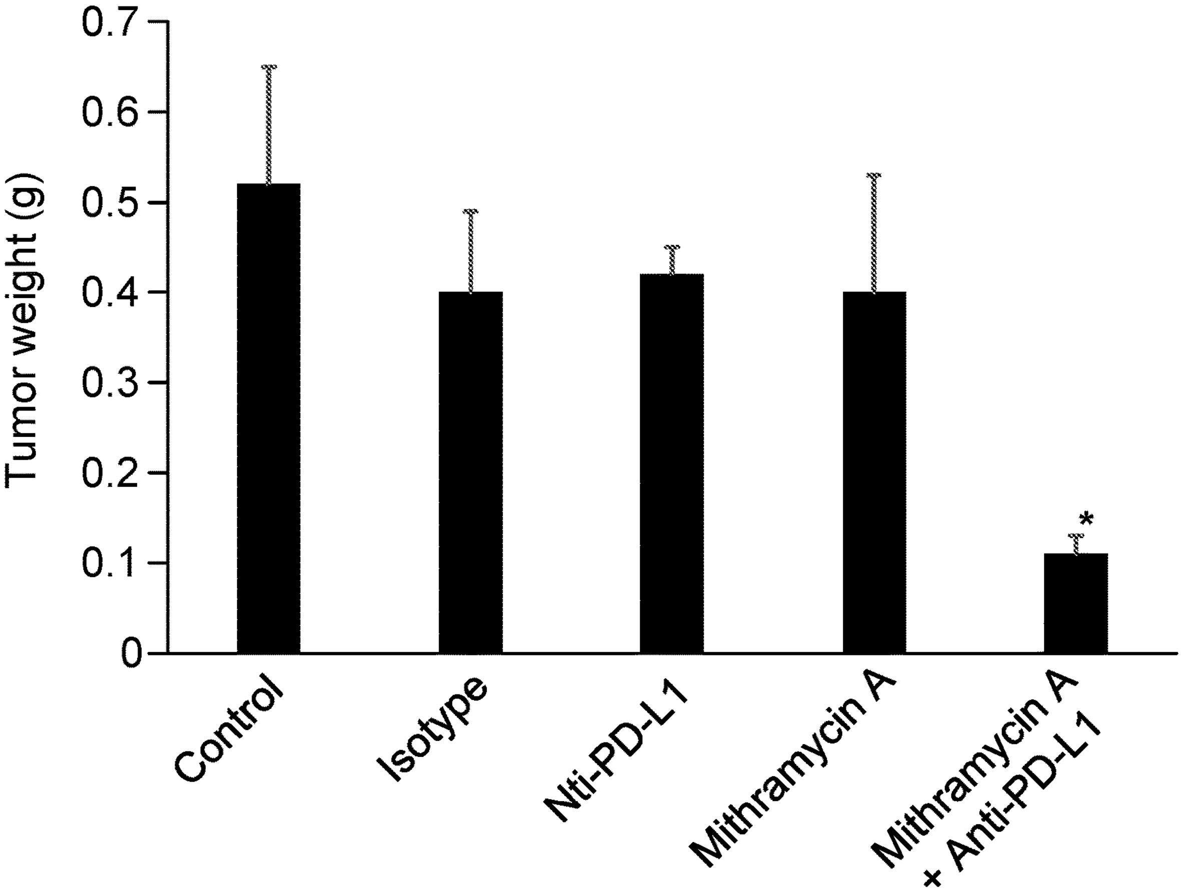
FIG. 11 depicts a bar graph showing tumor weight after the indicated treatments.

Combination of Mit-A and αPD-L1 induces potent anti-tumor response in MC-38 tumor model. MC-38 mouse tumor cells (p53 mutant, K-RAS wild-type, MSI-H)[31] ($10^6$/mouse) were implanted subcutaneously into the flank of C57BL/6 mice (n=6). Mice received 200 μg/mouse of αPD-L1 or isotype antibody and/or Mit-A (1 mg/kg) i.p. on days 8,10, 12 and 14. Intraperitoneal injection of Mit-A of 1 mg/kg/day starting on day 8 inhibited the tumor growth (FIG. 6A). The body weight did not change significantly between the groups during the course of the treatment (not shown), suggesting the negligible toxicity of Mit-A on these mice. ICIs are a major class of CIx with great potential as cancer therapeutics[20,21,22]. Since ICIs have shown moderate effectiveness in CRCs, in a pilot study, the effects of Mit-A in modulating response to a prototype ICI, αPD-L1 were evaluated. αPD-L1 (10F.9G2) (BioXCell) treatment was initiated on day 8 and; the αPD-L1 antibody but not isotype reduced MC-38 tumor volume (FIG. 6A). Moreover, combination treatment (αPD-L1 plus Mit-A) in mice promoted significantly greater inhibition of tumor growth (FIG. 6A) and tumor weight (FIG. 11). Anti-tumor activity of the combination treatment was correlated with a reduction in Ki-67 (proliferation marker, not shown), and Lgr5 expression (stem ness marker) and infiltration of T cells (FIG. 6B). Moreover, combination regimen induced E-cadherin (which targets CSCs by promoting mesenchymal to epithelial transition), IL12 p70 (which promotes activation of DCs), and Granzyme B (which promotes CTL-mediated killing) and reduced expression of Pro-MMP9 (which inhibits tumor growth) and immune checkpoint protein CTLA4. Bar graphs represent mean fold change±SD (FIG. 6C). Also, flow cytometry analysis suggest that the combination treatment differentiated MDSCs to a monocytic lineage (m-MDSC) (FIG. 6E) and significantly reduced the expression of PD-L1 expression among DCs and m-MDSCs, suggesting that host PDL-1 expression is crucial for tumor growth (FIG. 6D, E). Data indicate mean±SEM. One-Way ANOVA with post-hoc test used for comparison. *p≤0.05, **p≤0.01.

Example 7

Mit-A and αPD-L1 treatment inhibited the ex vivo colon tumor growth: One feature of the tumoroid culture is that tumor biopsy when cultured ex vivo on scaffold retains stromal cells, such as CAFs, immune cells and endothelial cells even after 6 days of culture[9, 10]. Since tumor microenvironment modulates the responsiveness to drugs in vivo, the growth inhibition potential of Mit-A and/or αPD-L1 treatment was evaluated ex vivo in MC-38 and HT-29 tumoroids. A single cell suspension of tumors isolated from mice was cultured ex vivo on the scaffold, which formed tumoroids (FIG. 7A). A comparison of gene expression profiles of in vivo MC38 tumors with ex vivo tumoroids using PANTHER's gene list analyses showed a high degree of co-related clustering (~70%), indicating that gene expression (involved in angiogenesis, apoptosis, cell cycle, DNA damage & repair, EMT, hypoxia signaling, and metabolism) remained unchanged (<2.0-fold) in the tumoroids even after 7 days in culture ex vivo (data not shown). Further, the expansion of the rare CSC population from in vivo tumors was examined. Flow cytometry data showed a 2.8-fold increase in ALDH activity in the tumoroids derived from MC38 tumors compared to monolayer (FIG. 7B; 17.6% in tumoroids vs. 6.7% in monolayer). Day 4 tumoroids were treated with indicated drugs for 48 hours and assayed by CellTiter-Glo. *p≤0.05. (FIGS. 7C and 7D). Mit-A and αPD-L1 treatment significantly inhibited the growth of ex vivo MC-38 tumoroids better than either treatment alone (FIG. 7C). Ex vivo data corroborated in vivo data presented in FIG. 9, suggesting that tumoroid platform can be used to assess the effects of ICx and/or Mit-A. Similarly, ex vivo culture of HT29 tumoroids was established from a single cell suspension of HT29 xenografted tumors established by inoculation of HT29 ($3.5\times10^6$) into the flank of nude mice in Matrigel. Treatment of Mit-A, but not FUOX reduced the growth of ex vivo HT-29 tumoroids (FIG. 7D) in a dose-dependent manner.

Example 8

Mit-A inhibited the in vivo CT-26 tumor growth: The effects of Mit-A in CT-26 cells that are aggressive in carcinogenesis (MSS) and metastasize to the liver upon splenic injection was investigated[32]. BALB/c mice (n=3) were injected subcutaneously in the right flank with CT26 cells ($5\times10^5$/mouse). Seven days after tumor inoculation, mice were treated daily with 1 mg/kg of Mit-A injected i.p. CT-26 tumor cells ($5\times10^5$/mouse) on days 8, 10 and 12. This demonstrates that Mit-A treatment significantly reduced CT-26 tumor volume (FIG. 8A) and tumor weight (FIG. 8B). qPCR analysis also confirmed that Mit-A inhibition of the CT26 tumor growth correlated to the reduced expression of CD133 (FIG. 8C) suggesting that Mit-A targets CSCs in vivo. *P<0.05 ***P<0.001

Example 9

Mit-A potentiates the inhibitory effects of transforming growth factor β (TGFβ): TGFβ activated stroma is one of the defining features of MSS CRCs[33]. These tumors do not respond to ICIs in part due to presence of increased TGFβ in the TME that causes immune evasion[34]. However, inhibition of TGFβ in these tumors induced a potent anti-tumor response. Since Sp1 is implicated in TGFβ induced tumor invasion, whether inhibition of TGFβ signaling will promote sensitization of CT26 cells to Mit-A was examined. Treatment of CT26 cells with a dual kinase inhibitor of TGFβ type I and II receptors (TGFβI), LY2109761 (Selleck) by itself did not inhibit CT26 cell viability, however a combination of both Mit-A and TGFβI significantly reduced cell viability (FIG. 9), suggesting that a TGFβI has potential for synergistic response for aggressive CRCs.

Example 10

Figures 12A, 12B:
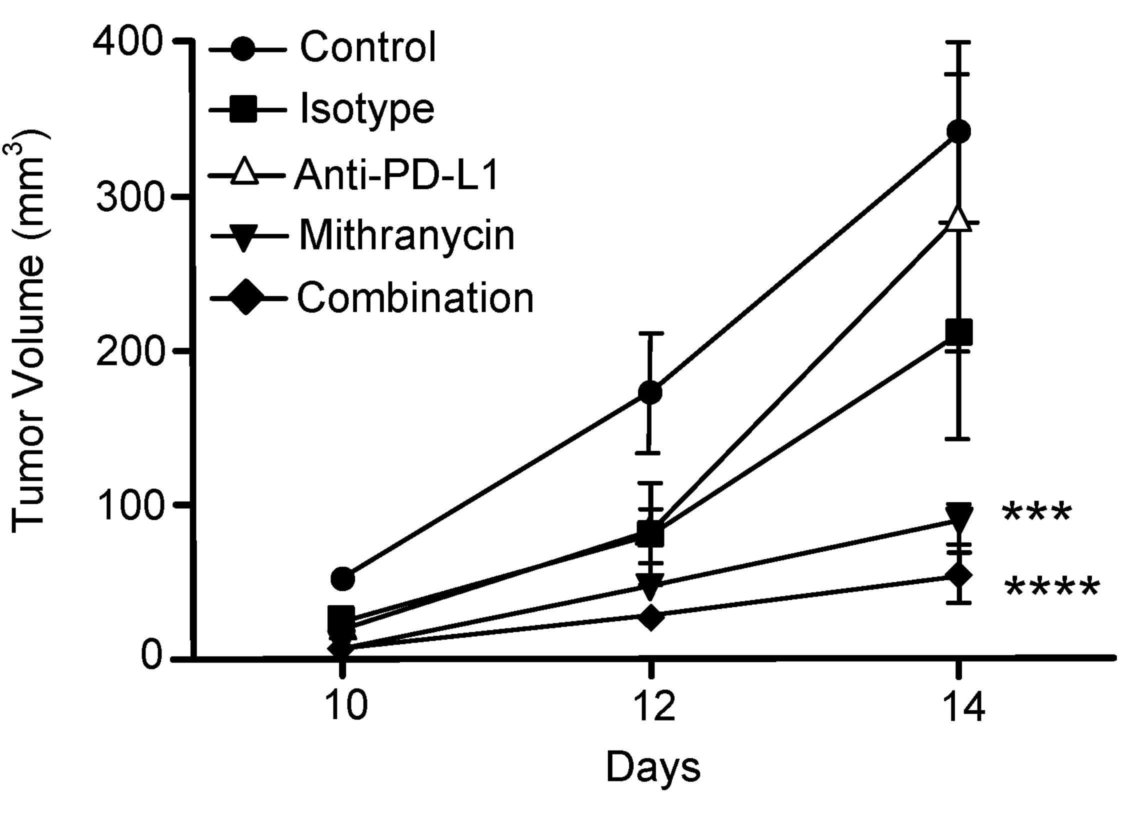
FIG. 12A depicts a plot of tumor volume on days 10, 12, and 14 for various treatments.
FIG. 12B depicts a bar graph of tumor weight for various treatments.
Figure 12C:
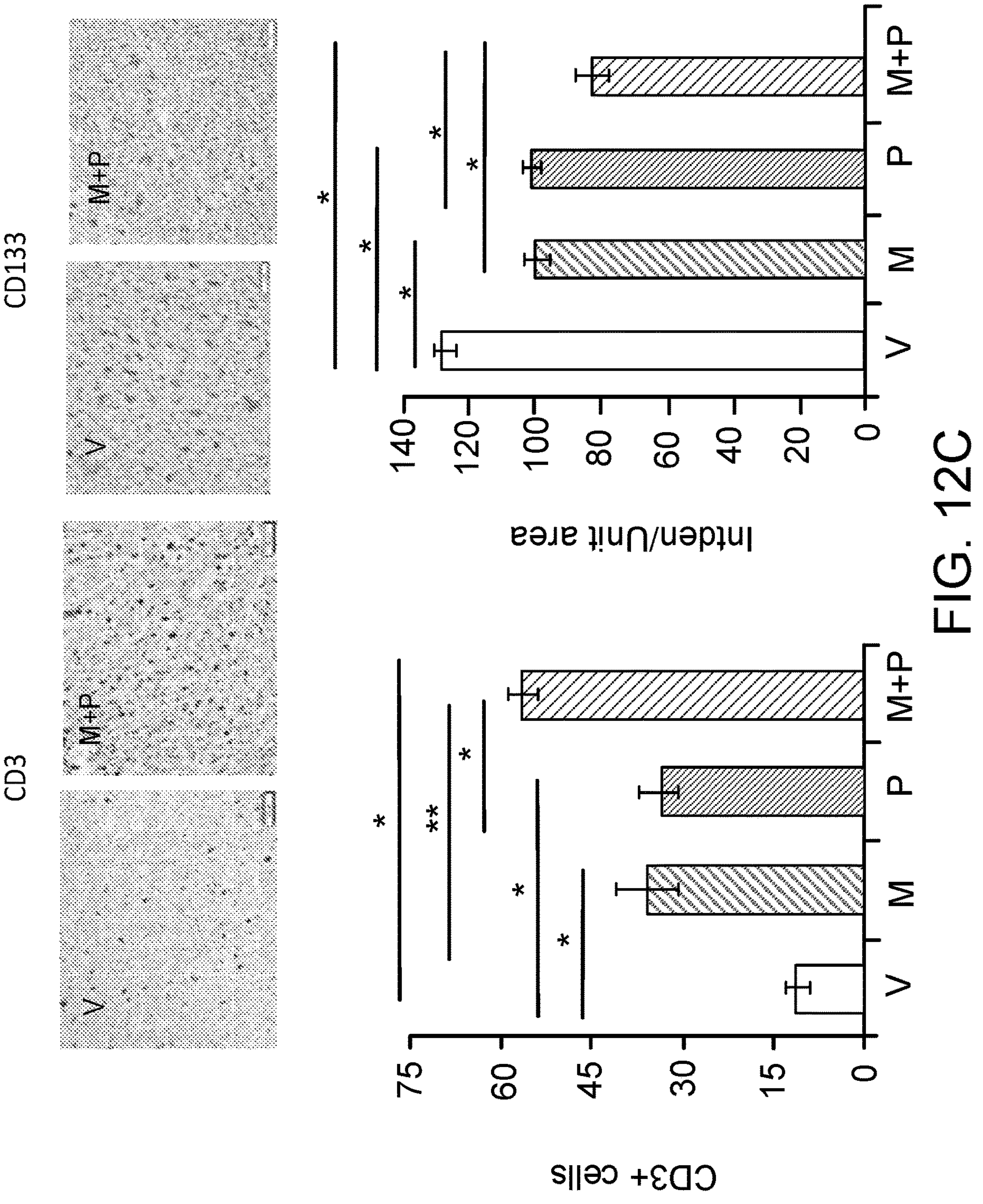
FIG. 12C depicts IHC of a representative section from the vehicle (V) and Mit-A (M), anti-PDL1 (P) treated tumors is shown. Bar graphs represent the average (5 fields/tumor section; n=2) number±SD of cells stained for T cells (using anti-CD3) and CD133.
Figure 12D:
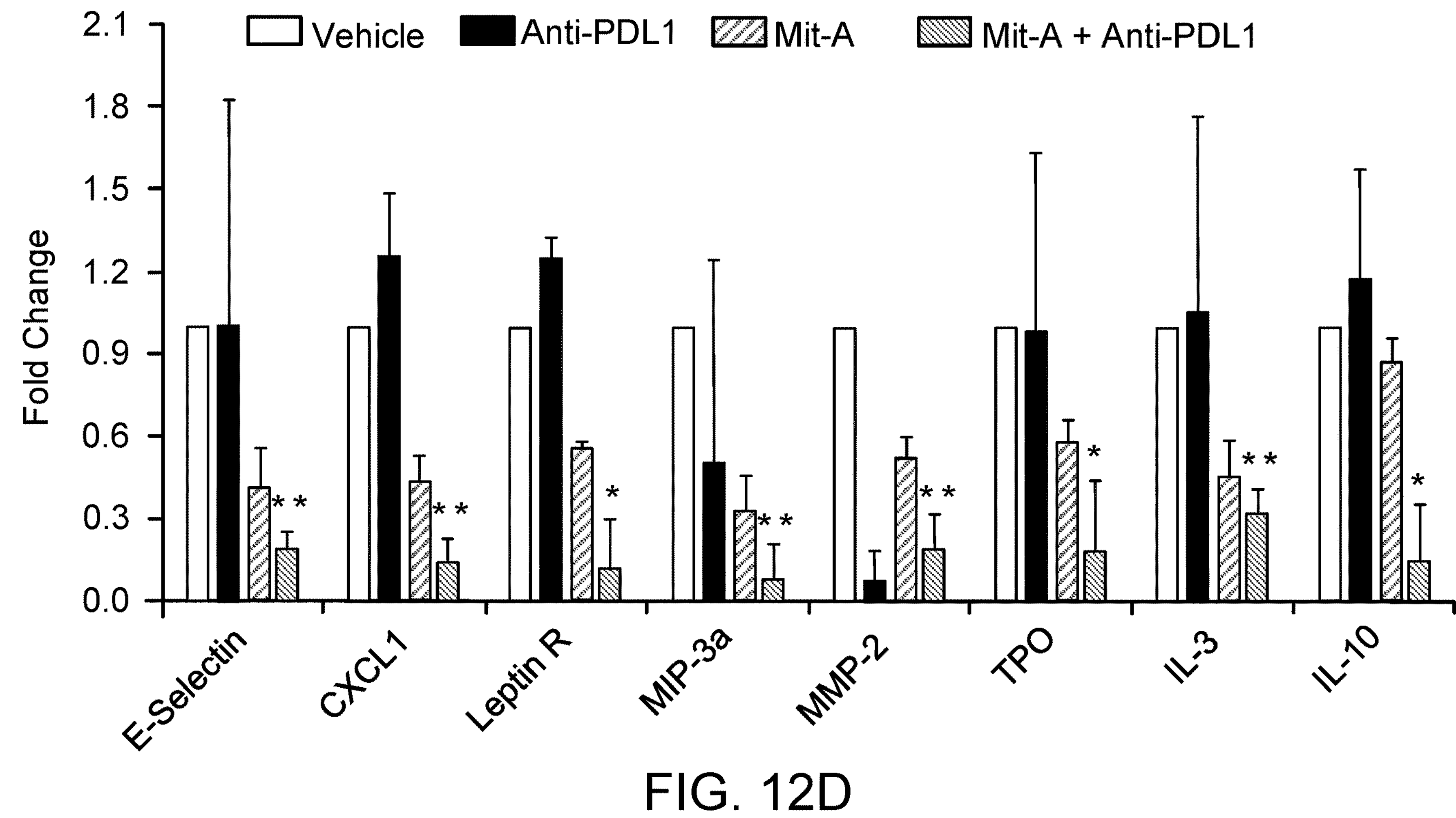
FIG. 12D depicts a bar graph of mouse cytokines and chemokines in tumor lysates of a control, αPD-L1, Mit-A, and combination of Mit-A+ Anti-PDL1.
Figure 12E:
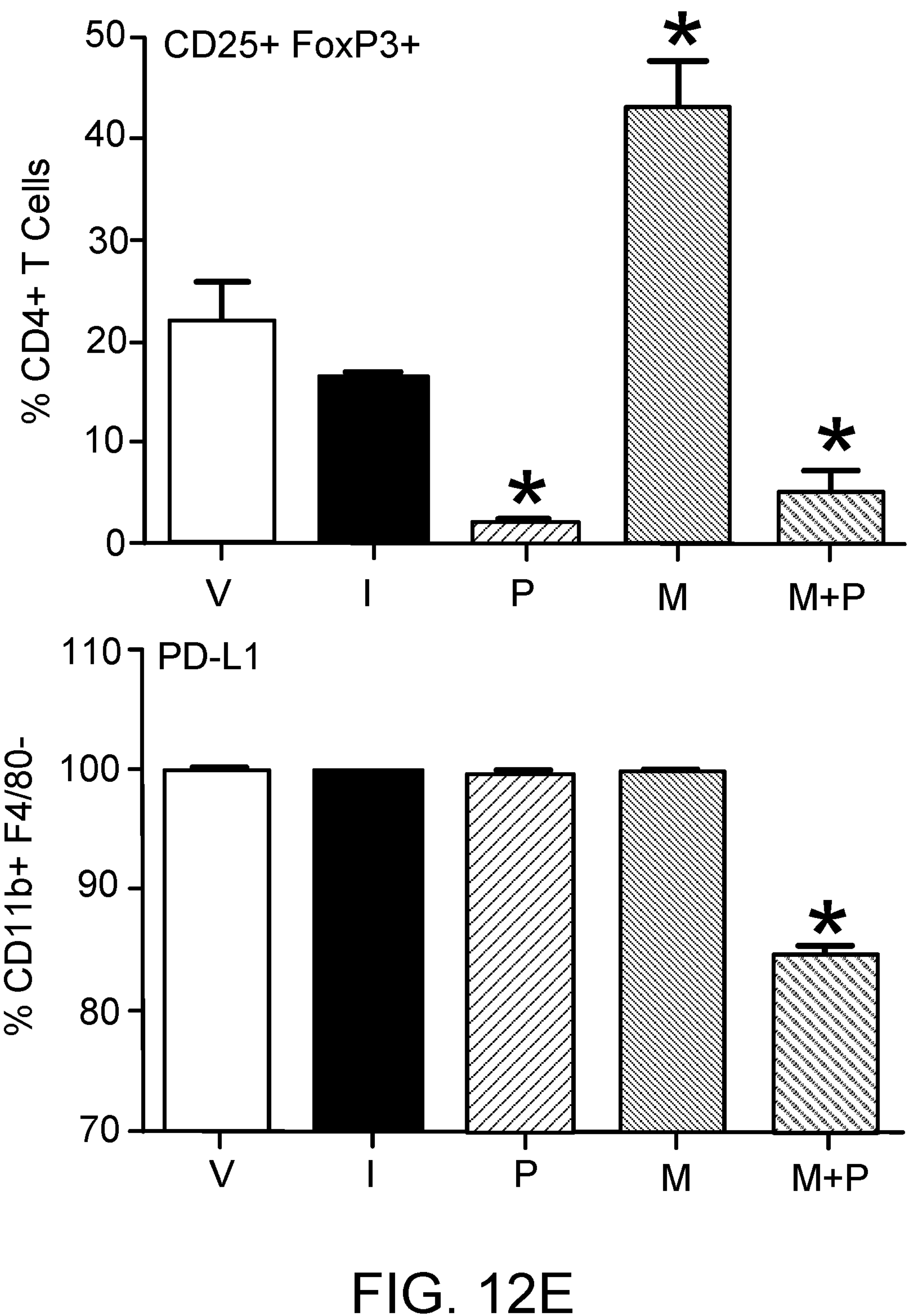
FIG. 12E depicts bar graphs showing the number of CD4+T cells expressing FoxP3+ Tregs and PDL1 expression in CD11b+F4/80+ (MΦ). (n=4).

Antineoplastic effect of Mit-A and anti-PDL1 in vivo: To determine the antineoplastic effect of Mit-A and anti-PDL1 in vivo, an immunocompetent syngeneic CT26 mouse model of colon adenocarcinoma that is aggressive in carcinogenesis (MSS) was used which metastasizes to the liver upon splenic injection. BALB/c mice (n=6) were injected subcutaneously in the right flank with CT26 cells ($5\times10^5$/mouse). Eight days after tumor inoculation, mice were treated every other day with 1 mg/kg of Mit-A injected i.p. (Mice received 200 μg/mouse of αPD-L1 or isotype antibody and/or Mit-A (1 mg/kg) i.p. on days 8, 10, 12 and 14). The results showed that Mit-A treatment significantly reduced CT26 tumor volume as measured by caliper (FIG. 12A) and tumor weight (FIG. 12B). The body weight did not change significantly between the groups during the course of the treatment suggesting the negligible toxicity of Mit-A on these mice. qPCR analysis also confirmed that Mit-A inhibition of the CT26 tumor growth correlated to the reduced expression of CD133 suggesting that Mit-A targets CSCs in vivo. A αPD-L1 (10F.9G2) (BioXCell) treatment (200 μg) was initiated on day 8 and demonstrated that αPD-L1 antibody did not significantly reduce CT26 tumor volume (FIG. 12A). However, the combination treatment of αPD-L1 and Mit-A (referred to herein as "comboRx") in mice promoted significantly greater inhibition (additive effect) of tumor growth (FIG. 12A) and tumor weight (FIG. 12B). Anti-tumor activity of the comboRx was correlated with the recruitment of T cells (CD3), reduction in CSC population (CD133 and Lgr5) (FIG. 12C) and cell proliferation (Ki67) in the tumor sections. A semiquantitative assessment of mouse cytokines/chemokines in tumor lysates of control, αPD-L1, Mit-A, or combination (M+P) (n=2) using mouse cytokine array C1 (RayBiotech) was also performed (FIG. 12D). Bar graphs represent mean fold change±SD. Only the comboRx but not single regimen inhibited expression of inflammatory factors associated with metastatic CRCs (CXCL1, MIP3α, MMP2 and TPO), increased tumor cell migration (E-selectin), and neoangiogenesis (Leptin receptor (Leptin-R)) (FIG. 12D). Also, comboRx significantly reduced the expression of IL-3 (associated with increased colon cancer risk) and IL-10 (associated with increased recurrence and worse prognosis) (FIG. 12D). Further, flow cytometry analysis of single cell suspension of tumors suggests that while Mit-A treatment induced tumor infiltration by immunosuppressive FoxP3+ Tregs, α-PDL1 and comboRx significantly reduced Tregs (FIG. 12E). Moreover, comboRx significantly increased differentiation of MDSCs to a granulocytic (g-MDSC) lineage (% of CD11B+ cells that are Ly6G+: Vehicle: 5%; α-PDL1: 15%; comboRx: 25%) and reduced PD-L1 expression among DCs and MΦs, suggesting that PDL-1 antibody treatment is affecting at least DCs and MΦs (FIG. 12E). Data indicate mean±SEM. One-Way ANOVA with posthoc test used for comparison. *p≤0.05, p≤0.01, *p≤0.001.

REFERENCES

1. Clarke M F, Dick J E, Dirks P B, et al. Cancer stem cells—perspectives on current status and future directions: AACR Workshop on cancer stem cells. Cancer research. 2006; 66(19):9339-44. doi: 10.1158/0008-5472.CAN-06-3126. PubMed PMID: 16990346.
2. Reya T, Morrison S J, Clarke M F, et al. Stem cells, cancer, and cancer stem cells. Nature. 2001; 414(6859): 105-11. Epub 2001 Nov. 2. doi: 10.1038/35102167. PubMed PMID: 11689955.
3. Veglia F, Perego M, Gabrilovich D. Myeloid-derived suppressor cells coming of age. Nature immunology. 2018; 19(2):108-19. Epub 2018 Jan. 20. doi: 10.1038/s41590-017-0022-x. PubMed PMID: 29348500.
4. Nagaraj S, Gupta K, Pisarev V, et al. Altered recognition of antigen is a novel mechanism of CD8+ T cell tolerance in cancer Nat Med. 2007; 13:828-35.
5. Wu X, Zhang H, Xing Q, et al. PD-1(+) CD8(+) T cells are exhausted in tumours and functional in draining lymph nodes of colorectal cancer subjects. Br J Cancer. 2014; 111(7):1391-9. Epub 2014 Aug. 6. doi: 10.1038/bjc.2014.416. PubMed PMID: 25093496; PMCID: PMC4183848.
6. Peng D, Tanikawa T, Li W, et al. Myeloid-Derived Suppressor Cells Endow Stem-like Qualities to Breast Cancer Cells through IL6/STAT3 and NO/NOTCH Cross-talk Signaling. Cancer research. 2016; 76(11):3156-65. Epub 2016 May 20. doi: 10.1158/0008-5472.CAN-15-2528. PubMed PMID: 27197152; PMCID: PMC4891237.
7. Panni R Z, Sanford D E, Belt B A, et al. Tumor-induced STAT3 activation in monocytic myeloid-derived suppressor cells enhances stemness and mesenchymal properties in human pancreatic cancer. Cancer immunology, immunotherapy : CII. 2014; 63(5):513-28. Epub 2014 Mar. 22. doi: 10.1007/s00262-014-1527-x. PubMed PMID: 24652403; PMCID: PMC3994288.
8. Zhang B, Wang Z, Wu L, et al. Circulating and tumor-infiltrating myeloid-derived suppressor cells in subjects with colorectal carcinoma. PloS one. 2013; 8(2):e57114. Epub 2013 Feb. 26. doi: 10.1371/journal.pone.0057114. PubMed PMID: 23437326; PMCID: PMC3577767.
9. Girard Y K, Wang C, Ravi S, et al. A 3D fibrous scaffold inducing tumoroids: a platform for anticancer drug development. PLoS One. 2013; 8(10):e75345. Epub 2013 Oct. 23. doi: 10.1371/journal.pone.0075345. PubMed PMID: 24146752; PMCID: PMC3797770.
10. Nair R, Padhee, S., Das, T., Green, R., Howell, M., Mohapatra, S. S. and Mohapatra, S. Three- and Four-dimensional Spheroid and FiSS Tumoroid Cultures: Platforms for Drug Discovery and Development, and Translational Research. Critical reviews in Therapeutic Drug Carrier Systems. 2017 34 (3): 185-208. doi: 10.1615/CritRevTherDrugCarrierSyst.2017018042.
11. Das T, Nair R R, Green R, et al. Actinomycin D Down-regulates SOX2 Expression and Induces Death in Breast Cancer Stem Cells. Anticancer research. 2017; 37(4):1655-63. doi: 10.21873/anticanres.11496. PubMed PMID: 28373426.
12. Chen J, Xia Q, Jiang B, et al. Prognostic Value of Cancer Stem Cell Marker ALDH1 Expression in Colorectal Cancer: A Systematic Review and Meta-Analysis. PLoS One. 2015; 10(12):e0145164. Epub 2015 Dec. 20. doi: 10.1371/journal.pone.0145164. PubMed PMID: 26682730; PMCID: PMC4686173.
13. Mohapatra S S B S, Bouvet M, Cosman B, Goel A, Kelley M, Mishra L, White J, Rao S, Jogunoori W, Mishra B, Bharadwaj S, Vidyarthi G, Mohapatra S, Patel B, Pisegna J, Scheuner M, Raufman J, Roy H and Singh S. Precision Medicine for CRC Subjects in the Veteran Population: State-of-the-Art, Challenges and Research Directions Digestive Diseases and Sciences. 2018:(in Press).
14. Scatena R, Bottoni P, Pontoglio A, et al. Cancer stem cells: the development of new cancer therapeutics. Expert Opin Biol Ther. 2011; 11(7):875-92. Epub 2011 Apr. 6. doi: 10.1517/14712598.2011.573780. PubMed PMID: 21463158.
15. Brown J H, Kennedy B J. Mithramycin in the Treatment of Disseminated Testicular Neoplasms. N Engl J Med. 1965; 272:111-8. Epub 1965 Jan. 21. doi: 10.1056/NEJM196501212720301. PubMed PMID: 14224214.
16. Previdi S, Malek A, Albertini V, et al. Inhibition of Sp1-dependent transcription and antitumor activity of the new aureolic acid analogues mithramycin SDK and SK in human ovarian cancer xenografts. Gynecol Oncol. 2010; 118(2):182-8. Epub 2010 May 11. doi: 10.1016/j.ygyno.2010.03.020. PubMed PMID: 20452660; PMCID: PMC2900446.
17. Yang W J, Song M J, Park E Y, et al. Transcription factors Sp1 and Sp3 regulate expression of human ABCG2 gene and chemoresistance phenotype. Mol Cells. 2013; 36(4): 368-75. Epub 2013 Sep. 3. doi: 10.1007/s10059-013-0191-x. PubMed PMID: 23996530; PMCID: PMC3887993.
18. Llosa N J, Cruise M, Tam A, et al. The vigorous immune microenvironment of microsatellite instable colon cancer is balanced by multiple counter-inhibitory checkpoints. Cancer Discov. 2015; 5(1):43-51. Epub 2014 Nov. 2. doi: 10.1158/2159-8290.CD-14-0863. PubMed PMID: 25358689; PMCID: PMC4293246.

19. Le D T, Uram J N, Wang H, et al. PD-1 Blockade in Tumors with Mismatch-Repair Deficiency. N Engl J Med. 2015; 372(26):2509-20. doi: 10.1056/NEJMoa1500596. PubMed PMID: 26028255; PMCID: PMC4481136.

20. Chung K Y, Gore I, Fong L, et al. Phase II study of the anti-cytotoxic T-lymphocyte-associated antigen 4 monoclonal antibody, tremelimumab, in subjects with refractory metastatic colorectal cancer. J Clin Oncol. 2010; 28(21):3485-90. doi: 10.1200/JCO.2010.28.3994. PubMed PMID: 20498386.

21. Topalian S L, Hodi F S, Brahmer J R, et al. Safety, activity, and immune correlates of anti-PD-1 antibody in cancer. N Engl J Med. 2012; 366(26):2443-54. doi: 10.1056/NEJMoa1200690. PubMed PMID: 22658127; PMCID: PMC3544539.

22. Brahmer J R, Tykodi S S, Chow L Q, et al. Safety and activity of anti-PD-L1 antibody in subjects with advanced cancer. N Engl J Med. 2012; 366(26):2455-65. doi: 10.1056/NEJMoa1200694. PubMed PMID: 22658128; PMCID: PMC3563263.

23. Signorini L, Delbue S, Ferrante P, et al. Review on the immunotherapy strategies against metastatic colorectal carcinoma. Immunotherapy. 2016; 8(10):1245-61. doi: 10.2217/imt-2016-0045. PubMed PMID: 27605072.

24. Bever K M, Le D T. An Expanding Role for Immunotherapy in Colorectal Cancer. J Natl Compr Canc Netw. 2017; 15(3):401-10. Epub 2017 Mar. 10. PubMed PMID: 28275038.

25. Castle J C, Loewer M, Boegel S, et al. Immunomic, genomic and transcriptomic characterization of CT26 colorectal carcinoma. BMC Genomics. 2014; 15:190. Epub 2014 Mar. 14. doi: 10.1186/1471-2164-15-190. PubMed PMID: 24621249; PMCID: PMC4007559.

26. Wohlert S E, Kunzel E, Machinek R, et al. The structure of mithramycin reinvestigated. J Nat Prod. 1999; 62(1): 119-21. Epub 1999 Jan. 23. doi: 10.1021/np980355k. PubMed PMID: 9917296.

27. Dutcher J P, Coletti D, Paietta E, et al. A pilot study of alpha-interferon and plicamycin for accelerated phase of chronic myeloid leukemia. Leuk Res. 1997; 21(5):375-80. Epub 1997 May 1. PubMed PMID: 9225062.

28. Lin R K, Hsu C H, Wang Y C. Mithramycin A inhibits DNA methyltransferase and metastasis potential of lung cancer cells. Anticancer Drugs. 2007; 18(10):1157-64. Epub 2007 Sep. 26. doi: 10.1097/CAD.0b013e3282a215e9. PubMed PMID: 17893516.

29. Choi E S, Nam J S, Jung J Y, et al. Modulation of specificity protein 1 by mithramycin A as a novel therapeutic strategy for cervical cancer. Sci Rep. 2014; 4:7162. Epub 2014 Nov. 25. doi: 10.1038/srep07162. PubMed PMID: 25418289; PMCID: PMC4241519.

30. Montico B, Nigro A, Casolaro V, et al. Immunogenic Apoptosis as a Novel Tool for Anticancer Vaccine Development. International journal of molecular sciences. 2018; 19(2). Epub 2018 Feb. 22. doi: 10.3390/ijms19020594. PubMed PMID: 29462947; PMCID: PMC5855816.

31. Efremova M, Rieder D, Klepsch V, et al. Targeting immune checkpoints potentiates immunoediting and changes the dynamics of tumor evolution. Nature communications. 2018; 9(1):32. Epub 2018 Jan. 4. doi: 10.1038/s41467-017-02424-0. PubMed PMID: 29296022; PMCID: PMC5750210.

32. Zhang B, Halder S K, Zhang S, et al. Targeting transforming growth factor-beta signaling in liver metastasis of colon cancer. Cancer letters. 2009; 277(1):114-20. Epub 2009 Jan. 17. doi: 10.1016/j.canlet.2008.11.035. PubMed PMID: 19147275; PMCID: PMC2776056.

33. Guinney J, Dienstmann R, Wang X, et al. The consensus molecular subtypes of colorectal cancer. Nature medicine. 2015; 21(11):1350-6. Epub 2015 Oct. 13. doi: 10.1038/nm.3967. PubMed PMID: 26457759; PMCID: PMC4636487.

34. Tauriello D V F, Palomo-Ponce S, Stork D, et al. TGFbeta drives immune evasion in genetically reconstituted colon cancer metastasis. Nature. 2018. doi: 10.1038/nature25492. PubMed PMID: 29443964.

What is claimed is:

1. A method of inhibiting metastasis of colorectal cancer in a patient in need thereof consisting of:

administering a therapeutically effective amount of a first compound wherein the first compound is mithramycin, or a pharmaceutically acceptable salt thereof, and a therapeutically effective amount of a second compound wherein the second compound is a dual kinase inhibitor targeting transforming growth factor β receptor type I and II, to a patient that has been diagnosed with colorectal cancer;

wherein the colorectal cancer is selected from the group consisting of microsatellite stable carcinoma, colorectal adenocarcinoma and colorectal sarcomas;

wherein the first compound is administered at a dose of about 0.5 mg/kg to about 10.0 mg/kg;

wherein the second compound is LY2109761 having a concentration of 5 μM;

wherein a combination of the therapeutically effective amounts of mithramycin, or a pharmaceutically acceptable salt thereof, and the second compound is effective in inhibiting metastasis of the colorectal cancer by inhibiting expression of inflammatory factors associated with metastatic colorectal cancers;

wherein the inflammatory factors are selected from the group consisting of C—X—C Motif Chemokine Ligand 1 (CXCL1), Macrophage Inflammatory Protein-3 (MIP3α), Matrix Metallopeptidase 2 (MMP2), Thrombopoietin (TPO), Interleukin-3 (IL-3) and Interleukin-10 (IL-10);

wherein the inflammatory factors are inhibited by about 10% to about 95% as compared to expression levels of the inflammatory factors prior to administration of the first and the second compounds; and wherein the combination of the mithramycin, or a pharmaceutically acceptable salt thereof, and the dual kinase inhibitor targeting transforming growth factor β receptor type I and II act synergistically to inhibit the metastases of the colorectal cancer of the patient.

2. The method of claim 1, wherein the colorectal cancer is microsatellite stable carcinoma.

3. The method of claim 1, wherein the mithramycin, or a pharmaceutically acceptable salt thereof, is administered at a dose of about 1 mg/kg.

4. A method of treating colorectal cancer in a subject in need thereof consisting of:

administering a therapeutically effective amount of mithramycin, or a pharmaceutically acceptable salt thereof, and a therapeutically effective amount of a dual kinase inhibitor targeting transforming growth factor β receptor type I and II, to a subject that has been diagnosed with colorectal cancer;

wherein the mithramycin, or a pharmaceutically acceptable salt thereof is administered at a dose of about 0.5 mg/kg to about 10.0 mg/kg;

wherein the dual kinase inhibitor targeting transforming growth factor β receptor type I and II is LY2109761 having a concentration of 5 μM;

wherein the colorectal cancer is selected from the group consisting of microsatellite stable carcinoma, colorectal adenocarcinoma, and colorectal sarcomas;

wherein the combination of the mithramycin, or a pharmaceutically acceptable salt thereof, and the LY2109761 act synergistically to inhibit colorectal cancer cell viability to treat the colorectal cancer of the subject.

* * * * *